United States Patent
Siekmann et al.

(10) Patent No.: US 10,350,301 B2
(45) Date of Patent: *Jul. 16, 2019

(54) BLOOD COAGULATION PROTEIN CONJUGATES

(71) Applicants: BAXALTA INCORPORATED, Bannockburn, IL (US); BAXALTA GMBH, Zug (CH)

(72) Inventors: Juergen Siekmann, Vienna (AT); Stefan Haider, Prinzersdorf (AT); Hanspeter Rottensteiner, Vienna (AT); Peter Turecek, Klosterneuburg (AT)

(73) Assignees: Baxalta Incorporated, Bannockburn, IL (US); Baxalta GmbH, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/249,657

(22) Filed: Aug. 29, 2016

(65) Prior Publication Data

US 2016/0361430 A1 Dec. 15, 2016

Related U.S. Application Data

(63) Continuation of application No. 14/988,931, filed on Jan. 6, 2016, now abandoned, which is a continuation of application No. 14/136,266, filed on Dec. 20, 2013, now abandoned, which is a continuation of application No. 12/843,542, filed on Jul. 26, 2010, now Pat. No. 8,637,640.

(60) Provisional application No. 61/347,136, filed on May 21, 2010, provisional application No. 61/228,828, filed on Jul. 27, 2009.

(51) Int. Cl.
| | |
|---|---|
| *C12N 9/96* | (2006.01) |
| *A61K 47/64* | (2017.01) |
| *C12N 9/64* | (2006.01) |
| *C08B 37/00* | (2006.01) |
| *A61K 38/48* | (2006.01) |
| *A61K 38/37* | (2006.01) |
| *C07K 1/107* | (2006.01) |
| *C07K 14/755* | (2006.01) |
| *A61K 47/60* | (2017.01) |
| *A61K 47/61* | (2017.01) |
| *A61K 47/62* | (2017.01) |
| *A61K 47/65* | (2017.01) |

(52) U.S. Cl.
CPC .......... *A61K 47/6455* (2017.08); *A61K 38/37* (2013.01); *A61K 38/4846* (2013.01); *A61K 47/60* (2017.08); *A61K 47/61* (2017.08); *A61K 47/62* (2017.08); *A61K 47/65* (2017.08); *C07K 1/1075* (2013.01); *C07K 14/755* (2013.01); *C08B 37/0006* (2013.01); *C12N 9/644* (2013.01); *C12N 9/6437* (2013.01); *C12N 9/96* (2013.01); *C12Y 304/21021* (2013.01); *C12Y 304/21022* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,757,006 A | 7/1988 | Toole, Jr. et al. |
| 4,966,999 A | 10/1990 | Coughlin et al. |
| 4,970,300 A | 11/1990 | Fulton et al. |
| 5,122,614 A | 6/1992 | Zalipsky |
| 5,153,265 A | 10/1992 | Shadle et al. |
| 5,198,349 A | 3/1993 | Kaufman |
| 5,198,493 A | 3/1993 | Holmberg et al. |
| 5,250,421 A | 10/1993 | Kaufman et al. |
| 5,298,643 A | 3/1994 | Greenwald |
| 5,492,821 A | 2/1996 | Callstrom et al. |
| 5,621,039 A | 4/1997 | Hallahan et al. |

(Continued)

FOREIGN PATENT DOCUMENTS

| | | |
|---|---|---|
| CA | 2647314 A1 | 11/2007 |
| EP | 0 306 968 A2 | 3/1989 |

(Continued)

OTHER PUBLICATIONS

Abuchowski et al., Cancer therapy with chemically modified enzymes. I. Antitumor properties of polyethylene glycol-asparaginase conjugates. *Cancer Biochem. Biophys.* 7: 175-86 (1984).
Baxter announces collaborations to develop longer acting forms of blood clotting factors. *Baxter News* (online), Sep. 29, 2005.
Bi et al., Target disruption of the mouse factor VIII gene produces a model of Haemophilia A. *Nat. Genet.* 10: 119-21 (1995).
Butenas et al., Potency and mass of factor VIII and FVIII products. *Haemophilia*, 15: 63-42 (2009).

(Continued)

*Primary Examiner* — Hope A Robinson
(74) *Attorney, Agent, or Firm* — Morgan, Lewis & Bockius LLP

(57) ABSTRACT

The invention relates to materials and methods of conjugating a water soluble polymer to an oxidized carbohydrate moiety of a blood coagulation protein comprising contacting the oxidized carbohydrate moiety with an activated water soluble polymer under conditions that allow conjugation. More specifically, the present invention relates to the aforementioned materials and methods wherein the water soluble polymer contains an active aminooxy group and wherein an oxime linkage is formed between the oxidized carbohydrate moiety and the active aminooxy group on the water soluble polymer. In one embodiment of the invention the conjugation is carried out in the presence of the nucleophilic catalyst aniline. In addition the generated oxime linkage can be stabilized by reduction with NaCNBH$_3$ to form an alkoxyamine linkage.

35 Claims, 8 Drawing Sheets

Specification includes a Sequence Listing.

(56) References Cited

U.S. PATENT DOCUMENTS

| | | | |
|---|---|---|---|
| 5,733,873 | A | 3/1998 | Osterberg et al. |
| 5,919,766 | A | 7/1999 | Osterberg et al. |
| 5,969,040 | A | 10/1999 | Hallahan et al. |
| 6,037,452 | A | 3/2000 | Minamino et al. |
| 6,048,720 | A | 4/2000 | Dalborg et al. |
| 6,183,738 | B1 | 2/2001 | Clark |
| 6,586,398 | B1 | 7/2003 | Kinstler et al. |
| 6,692,931 | B1 | 2/2004 | Reutter et al. |
| 6,743,908 | B2 | 6/2004 | Filpula et al. |
| 6,806,063 | B2 | 10/2004 | Pedersen et al. |
| 6,872,393 | B2 | 3/2005 | Whitlow et al. |
| 6,913,915 | B2 | 7/2005 | Ensor et al. |
| 7,118,737 | B2 | 10/2006 | Kochendoerfer et al. |
| 7,199,223 | B2 | 4/2007 | Bossard et al. |
| 7,230,081 | B1 | 6/2007 | Jensen et al. |
| 7,338,788 | B2 | 3/2008 | Pedersen et al. |
| 8,637,640 | B2 * | 1/2014 | Siekmann .......... A61K 47/4823 530/381 |
| 2002/0110535 | A1 | 8/2002 | Jones |
| 2003/0143596 | A1 | 7/2003 | Bentley et al. |
| 2004/0063911 | A1 | 4/2004 | DeFrees et al. |
| 2004/0126838 | A1 | 7/2004 | DeFrees et al. |
| 2004/0137557 | A1 | 7/2004 | DeFrees et al. |
| 2004/0142856 | A1 | 7/2004 | DeFrees et al. |
| 2004/0235734 | A1 | 11/2004 | Bossard et al. |
| 2005/0106658 | A1 | 5/2005 | DeFrees et al. |
| 2006/0019877 | A1 | 1/2006 | Conradt et al. |
| 2006/0088906 | A1 | 4/2006 | DeFrees et al. |
| 2006/0286634 | A1 | 12/2006 | Kingsman et al. |
| 2007/0105755 | A1 | 5/2007 | DeFrees et al. |
| 2007/0244301 | A1 | 10/2007 | Siekmann et al. |
| 2008/0146771 | A1 | 6/2008 | Kozlowski et al. |
| 2008/0260755 | A1 | 10/2008 | Metzner et al. |
| 2009/0076237 | A1 | 3/2009 | Turecek et al. |
| 2012/0076749 | A1 * | 3/2012 | Turecek ................. A61K 38/37 424/78.3 |

FOREIGN PATENT DOCUMENTS

| | | |
|---|---|---|
| EP | 0 605 963 A2 | 7/1994 |
| EP | 1 258 497 A2 | 11/2002 |
| EP | 1 260 582 A1 | 11/2002 |
| WO | WO 1991/009122 A2 | 6/1991 |
| WO | WO 1992/016555 A2 | 10/1992 |
| WO | WO 1994/005332 A2 | 3/1994 |
| WO | WO 1994/015625 A1 | 7/1994 |
| WO | WO 1994/028024 A1 | 12/1994 |
| WO | WO 1994/029370 A1 | 12/1994 |
| WO | WO 1995/001804 A1 | 1/1995 |
| WO | WO 1996/040731 A1 | 12/1996 |
| WO | WO 1996/041813 A2 | 12/1996 |
| WO | WO 1997/011957 A1 | 4/1997 |
| WO | WO 1999/028455 A1 | 6/1999 |
| WO | WO 1999/032134 A1 | 7/1999 |
| WO | WO 2000/012587 A1 | 3/2000 |
| WO | WO 2000/023114 A2 | 4/2000 |
| WO | WO 2000/048635 A1 | 8/2000 |
| WO | WO 2001/082943 A2 | 11/2001 |
| WO | WO 2001/083725 A1 | 11/2001 |
| WO | WO 2002/002764 A2 | 1/2002 |
| WO | WO 2002/022776 A2 | 3/2002 |
| WO | WO 2002/029025 A2 | 4/2002 |
| WO | WO 2002/077218 A1 | 10/2002 |
| WO | WO 2003/031464 A2 | 4/2003 |
| WO | WO 2003/045980 A2 | 6/2003 |
| WO | WO 2003/046150 A2 | 6/2003 |
| WO | WO 2004/000366 A1 | 12/2003 |
| WO | WO 2004/014424 A1 | 2/2004 |
| WO | WO 2004/030617 A1 | 4/2004 |
| WO | WO 2004/060965 A2 | 7/2004 |
| WO | WO 2004/075923 A2 | 9/2004 |
| WO | WO 2004/089280 A2 | 10/2004 |
| WO | WO 2004/108070 A2 | 12/2004 |
| WO | WO 2005/014024 A2 | 2/2005 |
| WO | WO 2005/014035 A2 | 2/2005 |
| WO | WO 2005/055950 A1 | 6/2005 |
| WO | WO 2005/070138 A2 | 8/2005 |
| WO | WO 2006/013202 A2 | 2/2006 |
| WO | WO 2006/016168 A2 | 2/2006 |
| WO | WO 2006/020372 A2 | 2/2006 |
| WO | WO 2006/053299 A2 | 5/2006 |
| WO | WO 2006/071801 A2 | 7/2006 |
| WO | WO 2006/074279 A1 | 7/2006 |
| WO | WO 2006/127896 A2 | 11/2006 |
| WO | WO 2006/134173 A2 | 12/2006 |
| WO | WO 2007/022784 A2 | 3/2007 |
| WO | WO 2007/076062 A2 | 7/2007 |
| WO | WO 2007/140282 A1 | 12/2007 |
| WO | WO 2008/012540 A1 | 1/2008 |
| WO | WO 2008/025856 A2 | 3/2008 |
| WO | WO 2008/035373 A2 | 3/2008 |
| WO | WO 2008/057683 A2 | 5/2008 |
| WO | WO 2008/074032 A1 | 6/2008 |
| WO | WO 2008/081024 A1 | 7/2008 |
| WO | WO 2008/119815 A1 | 10/2008 |
| WO | WO 2009/000522 A1 | 12/2008 |
| WO | WO 2009/006620 A1 | 1/2009 |
| WO | WO 2009/047500 A1 | 4/2009 |
| WO | WO 2009/089396 A2 | 7/2009 |
| WO | WO 2009/108806 A1 | 9/2009 |
| WO | WO 2009/130602 A2 | 10/2009 |
| WO | WO 2009/141418 A1 | 11/2009 |
| WO | WO 2009/141433 A1 | 11/2009 |
| WO | WO 2009/149303 A1 | 12/2009 |
| WO | WO 2010/010324 A1 | 1/2010 |
| WO | WO 2010/062768 A1 | 6/2010 |
| WO | WO 2010/083536 A1 | 7/2010 |
| WO | WO 2010/100430 A1 | 9/2010 |
| WO | WO 2010/102886 A1 | 9/2010 |
| WO | WO 2010/120365 A2 | 10/2010 |
| WO | WO 2010/131015 A1 | 11/2010 |
| WO | WO 2011/012850 A2 | 2/2011 |
| WO | WO 2011/014890 A1 | 2/2011 |
| WO | WO 2011/017055 A2 | 2/2011 |
| WO | WO 2011/018496 A2 | 2/2011 |
| WO | WO 2011/037896 A2 | 3/2011 |
| WO | WO 2011/064247 A1 | 6/2011 |
| WO | WO 2011/101242 A1 | 8/2011 |
| WO | WO 2011/101267 A1 | 8/2011 |
| WO | WO 2011/135307 A1 | 11/2011 |
| WO | WO 2011/135308 A1 | 11/2011 |
| WO | WO 2012/068134 A1 | 5/2012 |
| WO | WO 2013/009627 A2 | 1/2013 |

OTHER PUBLICATIONS

Caliceti et al., Pharmacokinetics of pegylated interferons: What is misleading? *Digest. Liver Dis.* 36(Suppl. 3): S334-9 (2004).
Cordes et al., Nucleophilic catalysis of semicarbazone formation by anilines. *J. Am. Chem. Soc.*, 84: 826-31 (1962).
Declaration of Juergen Siekmann, Ph.D., dated Apr. 4, 2013.
Declaration of Juergen Siekmann, Ph.D., dated Jun. 29, 2009.
Dirksen et al., Nucleophilic catalysis of hydrazone formation and transimination: Implications for dynamic covalent chemistry. *J. Am. Chem. Soc.*, 128: 15602-3 (2006).
Dirksen et al., Nucleophilic catalysis of oxime ligation. *Ange. Chem. Int. Ed.*, 45(45): 7581-4 (2006).
Dirksen et al., Rapid oxime and hydrazone ligations with aromatic aldehyres for biomolecular labeling. *Bioconj. Chem.*, 19(12): 2543-8 (2008).
El-Maarri et al., Functional analysis of the factor VIII B domain. 34th Hemophilia Symposium, pp. 324-337 (2005).
Enjolras et al., Two novel mutations in EGF-like domains of human factor IX dramatically impair intracellular processing and secretion. *J. Thromb. Haemost.* 2: 1143-54 (2003).
Geoghegan et al., Periodate inactivation of ovotransferrin and human serum transferrin. *J. Biol. Chem.* 255(27): 11429-34 (1980).
Great Britain Search Report and Written Opinion, GB-1012482.4, dated Nov. 24, 2010.
Gregoriadis et al., Improving the therapeutic efficacy of peptides and proteins: A role for polysialic acids. *Int. J. Pharmaceut.*, 300(1-2): 125-30 (2005).

(56) References Cited

OTHER PUBLICATIONS

Harris et al., Effect of pegylation on pharmaceuticals. *Nat. Rev. Drug Discovery.* 2: 214-21 (2003).
International Preliminary Report on Patentability, PCT/GB2010/001422, dated Jan. 31, 2012.
International Preliminary Report on Patentability, PCT/US2007/007560, dated Sep. 30, 2008.
International Preliminary Report on Patentability, PCT/US2009/052103, dated Feb. 1, 2011.
International Preliminary Report on Patentability, PCT/US2010/043242, dated Jan. 31, 2012.
International Preliminary Report on Patentability, PCT/US2011/045873, dated Feb. 5, 2013.
International Search Report and Written Opinion of the International Searching Authority, PCT/US2011/045873, European Patent Office, dated Nov. 24, 2011.
International Search Report and Written Opinion of the International Searching Authority, PCT/US2007/007560, European Patent Office, dated Sep. 18, 2007.
International Search Report and Written Opinion of the International Searching Authority, PCT/US2009/052103, European Patent Office, dated Feb. 12, 2010.
International Search Report and Written Opinion of the International Searching Authority, PCT/GB2010/001422, European Patent Office, dated Feb. 4, 2011.
International Search Report and Written Opinion, PCT/US2010/043242, dated Feb. 10, 2011.
Jain et al., Polysialylation: The natural way to improve the stability and pharmacokinestics of protein and peptide drugs <<http://www.lipoxen.co.uk/media/48760/dds%20and%20s%20pp3-9.pdf>>, dds &s, 4(1): 3-9 (2004).
Jenkins et al., Mutations associated with hemophilia A in the 558-565 loop of the factor VIIIa A2 subunit alter the catalytic activity of the factor Xase complex. *Blood*, 100(2): 501-8 (2002).
Jiang et al., Chemistry for pegylation of protein and peptide molecules, *Chin. J. Organ. Chem.*, 23(12): 1340-7 (2003).—English Abstract.
Kohler, Aniline: A catalyst for sialic acid detection. *ChemBioChem*, 10: 2147-50 (2009).
Kozlowski et al., Development of pegylated interferons for the treatment of chronic Hepatitis C. *BioDrugs.* 15(7): 419-29 (2001).
Lees et al., Versatile and efficient synthesis of protein-polysaccharide conjugate vaccines using aminooxy reagents and oxime chemistry. *Vaccine*, 24(6): 716-29 (2006).
Lenting et al., Factor VIII and von Willebrand factor—too sweet for their own good. *Haemophilia*, 16(Suppl. 5): 194-9 (2010).
Lenting et al., The life cycle of coagulation factor VIII in view of its structure and function. Blood, 92(11): 3983-96 (1998).
Mazsaroff et al., Quantitative comparison of global carbohydrate structures of glycoproteins using LC-MS and in-source fragmentation. Anal. Chem. 69(13): 2517-24 (1997).
Mukherjee et al., Structural analysis of factor IX protein variants to predict functional aberration causing haemophilia B. *Haemophilia*, 14(5): 1076-81 (2008).
Nektar Advanced PEGylation Catalog 2005-2006, p. 30 (2005).
Nektar Advanced PEGylation Price List 2005-2006, p. 11 (2005).
NOF Corporation DDS Catalogue, p. 58 (2005).
Parti et al., In vitro stability of recombinant human factor VIII (Recombinate®). *Haemophilia*, 6: 513-22 (2000).
Roberts et a., Chemistry for peptide and protein pegylation *Adv. Drug Del. Rev.* 54: 459-76 (2002).
Rosen et al., Assay of factor VIII: C with a chromogenic substrate. *Scand J. Haematol.* 33(Suppl. 40): 139-45 (1984).
Rostin et al., B-domain deleted recombinant coagulation factor VIII modified with monomethoxy polyethylene glycol. *Bioconjugate Chem.* 11: 387-96 (2000).
Saenko et al., Strategies towards a longer acting factor VIII. *Haemophilia.* 12: 42-51 (2006).
Sakuragawa et al., Studies on the stability of factor VIII modified by polyethylene glycol. *Acta Med. Biol.* 36: 1-5 (1988).
Schmidt et al., Structure-function relationships in factor IX and factor IXa. *Trends Cardiovasc. Med.* 13(1): 39-45 (2003).
Seffernick et al., Melamine deaminase and atrazine chlorohydrolase: 98% identical but functionally different. *J. Bacteriology.* 2405-10 (2001).
Severs et al., Characterization of PEGylated factor VIII molecules. *Blood.* 108: 11-12 (2006). Abstract.
Study shows molecular size and structure of PEG interferon molecules, as used in pegintron(R), affect antiviral activity in vitro. *Hispanic PR Wire*, Oct. 28, 2003.
Thygesen et al., Nucleophilic catalysis of carbohydrate oxime formation by anilines. *J. Org. Chem.*, 75: 1752-5 (2010).
Tsubery et al., Prolonging the action of protein and peptide drugs by a novel approach of reversible polyethylene glycol modification. *J. Biol. Chem.* 279(37): 38118-24 (2004).
Tsutsumi et al., Site-specific chemical modification with polyethylene glycol of recombinant immunotoxin anti-Tac(Fv)-PE38 (LMB-2) improves antitumor activity and reduces animal toxicity and immunogenicity. *Proc. Natl. Acad. Sci. USA.* 97: 8548-53 (2000).
Urrutigoity et al., Biocatalysis in organic solvents with a polymer-bound horseradish peroxidase. *Biocatalysis.* 2: 145-9 (1989).
Veronese et al., Bioconjugation in pharmaceutical chemistry. *IL Farmaco.* 54: 497-516 (1999).
Wells et al., Additivity of mutational effects in proteins. *Biochemistry.* 29(37): 8509-17 (1990).
Wilchek et al., Labeling glycoconjugates with hydrazide reagents. *Methods Enzymol.* 138: 429-42 (1987).
Yang et al., Expression, purification and characterization of factor IX derivatives using a novel vector system. *Protein Expr. Purif.* 50(2): 196-202 (2006).
Zalipsky et al., Hydrazide derivatives of poly(ethylene glycol) and their bioconjugates. Poly(ethylene glycol) Chemistry and Biological Applications. Chapter 21, pp. 318-341 (1997).
Zeng et al., High-efficency labeling of sialylated glycoproteins on living cells. *Nat. Methods*, 6(3): 207-9 (2009).

\* cited by examiner

SEQUENCE LISTING

<160> NUMBER OF SEQ ID NOS: 2

<210> SEQ ID NO 1
<211> LENGTH: 422
<212> TYPE: PRT
<213> ORGANISM: Homo sapiens

<400> SEQUENCE: 1

```
Leu Asn Arg Pro Lys Arg Tyr Asn Ser Gly Lys Leu Glu Glu Phe Val
1               5                   10                  15

Gln Gly Asn Leu Glu Arg Glu Cys Met Glu Glu Lys Cys Ser Phe Glu
            20                  25                  30

Glu Pro Arg Glu Val Phe Glu Asn Thr Glu Lys Thr Thr Glu Phe Trp
        35                  40                  45

Lys Gln Tyr Val Asp Gly Asp Gln Cys Glu Ser Asn Pro Cys Leu Asn
50                  55                  60

Gly Gly Ser Cys Lys Asp Asp Ile Asn Ser Tyr Glu Cys Trp Cys Pro
65                  70                  75                  80

Phe Gly Phe Glu Gly Lys Asn Cys Glu Leu Asp Val Thr Cys Asn Ile
                85                  90                  95

Lys Asn Gly Arg Cys Glu Gln Phe Cys Lys Asn Ser Ala Asp Asn Lys
            100                 105                 110

Val Val Cys Ser Cys Thr Glu Gly Tyr Arg Leu Ala Glu Asn Gln Lys
        115                 120                 125

Ser Cys Glu Pro Ala Val Pro Phe Pro Cys Gly Arg Val Ser Val Ser
130                 135                 140

Gln Thr Ser Lys Leu Thr Arg Ala Glu Ala Val Phe Pro Asp Val Asp
145                 150                 155                 160

Tyr Val Asn Pro Thr Glu Ala Glu Thr Ile Leu Asp Asn Ile Thr Gln
                165                 170                 175

Gly Thr Gln Ser Phe Asn Asp Phe Thr Arg Val Val Gly Gly Glu Asp
            180                 185                 190

Ala Lys Pro Gly Gln Phe Pro Trp Gln Val Val Leu Asn Gly Lys Val
        195                 200                 205

Asp Ala Phe Cys Gly Gly Ser Ile Val Asn Glu Lys Trp Ile Val Thr
210                 215                 220

Ala Ala His Cys Val Glu Thr Gly Val Lys Ile Thr Val Val Ala Gly
225                 230                 235                 240

Glu His Asn Ile Glu Glu Thr Glu His Thr Glu Gln Lys Arg Asn Val
                245                 250                 255

Ile Arg Ala Ile Ile Pro His His Asn Tyr Asn Ala Ala Ile Asn Lys
            260                 265                 270

Tyr Asn His Asp Ile Ala Leu Leu Glu Leu Asp Glu Pro Leu Val Leu
        275                 280                 285

Asn Ser Tyr Val Thr Pro Ile Cys Ile Ala Asp Lys Glu Tyr Thr Asn
290                 295                 300

Ile Phe Leu Lys Phe Gly Ser Gly Tyr Val Ser Gly Trp Ala Arg Val
305                 310                 315                 320

Phe His Lys Gly Arg Ser Ala Leu Val Leu Gln Tyr Leu Arg Val Pro
                325                 330                 335

Leu Val Asp Arg Ala Thr Cys Leu Arg Ser Thr Lys Phe Thr Ile Tyr
            340                 345                 350

Asn Asn Met Phe Cys Ala Gly Phe His Glu Gly Gly Arg Asp Ser Cys
        355                 360                 365
```

```
Gln Gly Asp Ser Gly Gly Pro His Val Thr Glu Val Glu Gly Thr Ser
    370             375             380

Phe Leu Thr Gly Ile Ile Ser Trp Gly Glu Glu Cys Ala Met Lys Gly
385             390             395             400

Lys Tyr Gly Ile Tyr Thr Lys Val Ser Arg Tyr Val Asn Trp Ile Lys
                405             410             415

Glu Lys Thr Lys Leu Thr
            420

<210> SEQ ID NO 2
<211> LENGTH: 5
<212> TYPE: PRT
<213> ORGANISM: Artificial Sequence
<220> FEATURE:
<223> OTHER INFORMATION: residue

<400> SEQUENCE: 2

Ala Leu Ile Val Pro
1               5
```

BLOOD COAGULATION PROTEIN CONJUGATES

This application is a Continuation of U.S. application Ser. No. 14/988,931 filed Jan. 6, 2016 (now abandoned), which is a Continuation of U.S. application Ser. No. 14/136,266 filed Dec. 20, 2013 (now abandoned), which is a Continuation of U.S. application Ser. No. 12/843,542 filed Jul. 26, 2010 (now issued as U.S. Pat. No. 8,637,640), which claims benefit of U.S. Provisional Application Ser. No. 61/347,136 filed May 21, 2010, and U.S. Provisional Application Ser. No. 61/228,828 filed Jul. 27, 2009, all of which are incorporated herein by reference in their entirety.

FIELD OF THE INVENTION

The present invention relates to materials and methods for conjugating a water soluble polymer to a blood coagulation protein.

REFERENCE TO A "SEQUENCE LISTING," A TABLE, OR A COMPUTER PROGRAM, LISTING APPENDIX SUBMITTED ON A COMPACT DISK

This invention incorporated by reference the Sequence Listing text copy submitted herewith, which was created on Nov. 30, 2017, entitled 008073_137_US03_ST25.txt which is 8 kilobytes in size.

BACKGROUND OF THE INVENTION

Therapeutic polypeptides such as blood coagulation proteins including Factor IX (FIX), Factor VIII (FVIII), Factor VIIa (FVIIa), Von Willebrand Factor (VWF), Factor FV (FV), Factor X (FX), Factor XI (FXI), Factor XII (FXII), thrombin (FII), protein C, protein S, tPA, PAI-1, tissue factor (TF) and ADAMTS 13 protease are rapidly degraded by proteolytic enzymes and neutralized by antibodies. This reduces their half-life and circulation time, thereby limiting their therapeutic effectiveness. Relatively high doses and frequent administration are necessary to reach and sustain the desired therapeutic or prophylactic effect of these coagulation proteins. As a consequence, adequate dose regulation is difficult to obtain and the need of frequent intravenous administrations imposes restrictions on the patient's way of living.

PEGylation of polypeptide drugs protects them in circulation and improves their pharmacodynamic and pharmacokinetic profiles (Harris and Chess, Nat Rev Drug Discov. 2003; 2:214-21). The PEGylation process attaches repeating units of ethylene glycol (polyethylene glycol (PEG)) to a polypeptide drug. PEG molecules have a large hydrodynamic volume (5-10 times the size of globular proteins), are highly water soluble and hydrated, non-toxic, non-immunogenic and rapidly cleared from the body. PEGylation of molecules can lead to increased resistance of drugs to enzymatic degradation, increased half-life in vivo, reduced dosing frequency, decreased immunogenicity, increased physical and thermal stability, increased solubility, increased liquid stability, and reduced aggregation. The first PEGylated drugs were approved by the FDA in the early 1990s. Since then, the FDA has approved several PEGylated drugs for oral, injectable, and topical administration.

Polysialic acid (PSA), also referred to as colominic acid (CA), is a naturally occurring polysaccharide. It is a homopolymer of N-acetylneuraminic acid with α(2→8) ketosidic linkage and contains vicinal diol groups at its non-reducing end. It is negatively charged and a natural constituent of the human body. It can easily be produced from bacteria in large quantities and with pre-determined physical characteristics (U.S. Pat. No. 5,846,951). Because the bacterially-produced PSA is chemically and immunologically identical to PSA produced in the human body, bacterial PSA is non-immunogenic, even when coupled to proteins. Unlike some polymers, PSA acid is biodegradable. Covalent coupling of colominic acid to catalase and asparaginase has been shown to increase enzyme stability in the presence of proteolytic enzymes or blood plasma. Comparative studies in vivo with polysialylated and unmodified asparaginase revealed that polysialylation increased the half-life of the enzyme (Fernandes and Gregoriadis, Biochimica Biophysica Acta 1341:26-34, 1997).

The preparation of conjugates by forming a covalent linkage between the water soluble polymer and the therapeutic protein can be carried out by a variety of chemical methods. For example, coupling of PEG-derivatives to peptides or proteins is reviewed by Roberts et al. (Adv Drug Deliv Rev 2002; 54:459-76). One approach for coupling water soluble polymers to therapeutic proteins is the conjugation of the polymers via the carbohydrate moieties of the protein. Vicinal hydroxyl (OH) groups of carbohydrates in proteins can be easily oxidized with sodium periodate (NaIO4) to form active aldehyde groups (Rothfus et Smith, J Biol Chem 1963; 238:1402-10; van Lenten et Ashwell, J Biol Chem 1971; 246:1889-94). Subsequently the polymer can be coupled to the aldehyde groups of the carbohydrate by use of reagents containing, for example, an active hydrazide group (Wilchek M and Bayer E A, Methods Enzymol 1987; 138:429-42). A more recent technology is the use of reagents containing aminooxy groups which react with aldehydes to form oxime linkages (WO 96/40662, WO2008/025856).

Additional examples describing conjugation of a water soluble polymer to a therapeutic protein are described in WO 06/071801 which teaches the oxidation of carbohydrate moieties in Von Willebrand factor and subsequent coupling to PEG using hydrazide chemistry; US Publication No. 2009/0076237 which teaches the oxidation of rFVIII and subsequent coupling to PEG and other water soluble polymers (e.g. PSA, HES, dextran) using hydrazide chemistry; WO 2008/025856 which teaches oxidation of different coagulation factors, e.g. rFIX, FVIII and FVIIa and subsequent coupling to e.g., PEG, using aminooxy chemistry by forming an oxime linkage; and U.S. Pat. No. 5,621,039 which teaches the oxidation of FIX and subsequent coupling to PEG using hydrazide chemistry.

Recently, an improved method was described comprising mild periodate oxidation of sialic acids to generate aldehydes followed by reaction with an aminooxy group containing reagent in the presence of catalytic amounts of aniline (Dirksen A et Dawson P E, Bioconjugate Chem. 2008; 19, 2543-8; and Zeng Y et al., Nature Methods 2009; 6:207-9). The aniline catalysis dramatically accelerates the oxime ligation, allowing the use of very low concentrations of the reagent.

Notwithstanding the methods available of conjugating water soluble polymers to therapeutic proteins, there remains a need to develop materials and methods for conjugating water soluble polymers to proteins that improves the protein's pharmacodynamic and/or pharmacokinetic properties while minimizing the costs associated with the various reagents.

SUMMARY OF THE INVENTION

The present invention provides materials and methods for conjugating polymers to proteins that improves the protein's pharmacodynamic and/or pharmacokinetic properties while minimizing the costs associated with the various reagents.

In one embodiment of the invention, a method of conjugating a water soluble polymer to an oxidized carbohydrate moiety of a blood coagulation protein comprising contacting the oxidized carbohydrate moiety with an activated water soluble polymer under conditions that allow conjugation; the blood coagulation protein selected from the group consisting of Factor IX (FIX), Factor VIII (FVIII), Factor VIIa (FVIIa), Von Willebrand Factor (VWF), Factor FV (FV), Factor X (FX), Factor XI (FXI), Factor XII (FXII), thrombin (FII), protein C, protein S, tPA, PAI-1, tissue factor (TF) and ADAMTS 13 protease or a biologically active fragment, derivative or variant thereof; the water soluble polymer containing an active aminooxy group and is selected from the group consisting of polyethylene glycol (PEG), branched PEG, polysialic acid (PSA), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), 2-methacryloyloxy-2'-ethyltrimethylammoniumphosphate (MPC); and the carbohydrate moiety oxidized by incubation with a buffer comprising an oxidizing agent selected from the group consisting of sodium periodate (NaIO4), lead tetraacetate (Pb(OAc)4) and potassium perruthenate (KRuO4); wherein an oxime linkage is formed between the oxidized carbohydrate moiety and the active aminooxy group on the water soluble polymer.

In another embodiment of the invention, the water soluble polymer according to the aforementioned method is PSA. In a related embodiment, the PSA is comprised of about 5-500 or 10-300 sialic acid units. In still another embodiment, the blood coagulation protein according to the aforementioned method is FIX. In another embodiment, the blood coagulation protein according to the aforementioned method is FVIIa. In still another embodiment, the blood coagulation protein according to the aforementioned method is FVIII. In yet another embodiment, the aforementioned method is provided wherein the oxidizing agent is sodium periodate (NaIO4). In another embodiment, the oxidized carbohydrate moiety of the blood coagulation protein according to the aforementioned method is located in the activation peptide of the blood coagulation protein.

In yet another embodiment of the invention, the aforementioned method is provided wherein the PSA is prepared by reacting an activated aminooxy linker with oxidized PSA;
wherein the aminooxy linker is selected from the group consisting of:
a 3-oxa-pentane-1,5-dioxyamine linker of the formula:

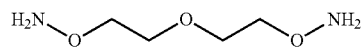

and
a 3,6,9-trioxa-undecane-1,11-dioxyamine linker of the formula:

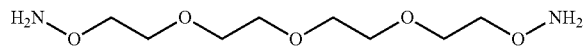 [SMILES: NOCCOCCOCCOCCON]

wherein the PSA is oxidized by incubation with a oxidizing agent to form a terminal aldehyde group at the non-reducing end of the PSA. In still another embodiment, the aforementioned method is provided wherein the activated aminooxy linker comprises 1-50 ethylene glycol units.

In still another embodiment, an aforementioned method is provided wherein the aminooxy linker is 3-oxa-pentane-1,5-dioxyamine. In a related embodiment, the oxidizing agent is NaIO$_4$.

In another embodiment of the invention, the aforementioned method is provided wherein the contacting of the oxidized carbohydrate moiety with the activated water soluble polymer occurs in a buffer comprising a nucleophilic catalyst selected from the group consisting of aniline and aniline derivatives.

In yet another embodiment of the invention, an aforementioned method is provided further comprising the step of reducing an oxime linkage in the conjugated blood coagulation protein by incubating the conjugated blood coagulation protein in a buffer comprising a reducing compound selected from the group consisting of sodium cyanoborohydride (NaCNBH3) and ascorbic acid (vitamin C). In a related embodiment the reducing compound is sodium cyanoborohydride (NaCNBH3).

In another embodiment of the invention, a modified blood coagulation protein produced by an aforementioned method is provided.

In still another embodiment of the invention, a modified FIX is provided comprising a FIX molecule or a biologically active fragment, derivative or variant thereof; and at least one aminooxy PSA bound to the FIX molecule, wherein said aminooxy PSA is attached to the FIX via one or more carbohydrate moieties.

In another embodiment of the invention, a modified FVIIa is provided comprising a FVIIa molecule or a biologically active fragment, derivative or variant thereof; and at least one aminooxy PSA bound to the FVIIa molecule, wherein said aminooxy PSA is attached to the FVIIa via one or more carbohydrate moieties.

In still another embodiment of the invention, a modified FVIII is provided comprising a FVIII molecule or a biologically active fragment, derivative or variant thereof; and at least one aminooxy PSA bound to the FVIII molecule, wherein said aminooxy PSA is attached to the FVIII via one or more carbohydrate moieties.

In still another embodiment of the invention, a modified FIX is provided comprising a FIX molecule or a biologically active fragment, derivative or variant thereof; and at least one aminooxy PEG bound to the FIX molecule, wherein said aminooxy PEG is attached to the FIX via one or more carbohydrate moieties.

In another embodiment of the invention, a modified FVIIa is provided comprising a FVIIa molecule or a biologically active fragment, derivative or variant thereof; and at least one aminooxy PEG bound to the FVIIa molecule, wherein said aminooxy PEG is attached to the FVIIa via one or more carbohydrate moieties.

In still another embodiment of the invention, a modified FVIII is provided comprising a FVIII molecule or a biologically active fragment, derivative or variant thereof; and at least one aminooxy PEG bound to the FVIII molecule, wherein said aminooxy PEG is attached to the FVIII via one or more carbohydrate moieties.

In yet another embodiment, a water soluble polymer is provided comprising an active aminooxy linker; said water soluble polymer selected from the group consisting of polyethylene glycol (PEG), branched PEG, polysialic acid (PSA), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG), polyoxazoline, poly acryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly (1-hydroxymethylethylene hydroxymethylformal) (PHF), 2-methacryloyloxy-2'-ethyltrimethylammoniumphosphate (MPC); said active aminooxy linker is selected from the group consisting of: a 3-oxa-pentane-1,5-dioxyamine linker of the formula:

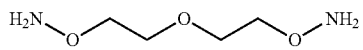

and a 3,6,9-trioxa-undecane-1,11-dioxyamine linker of the formula:

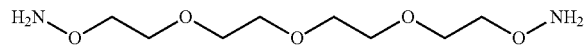

In still another embodiment, the aforementioned method is provided wherein activated aminooxy linker comprises 1-50 ethylene glycol units.

FIGURES

DETAILED DESCRIPTION OF THE INVENTION

Figure 1:
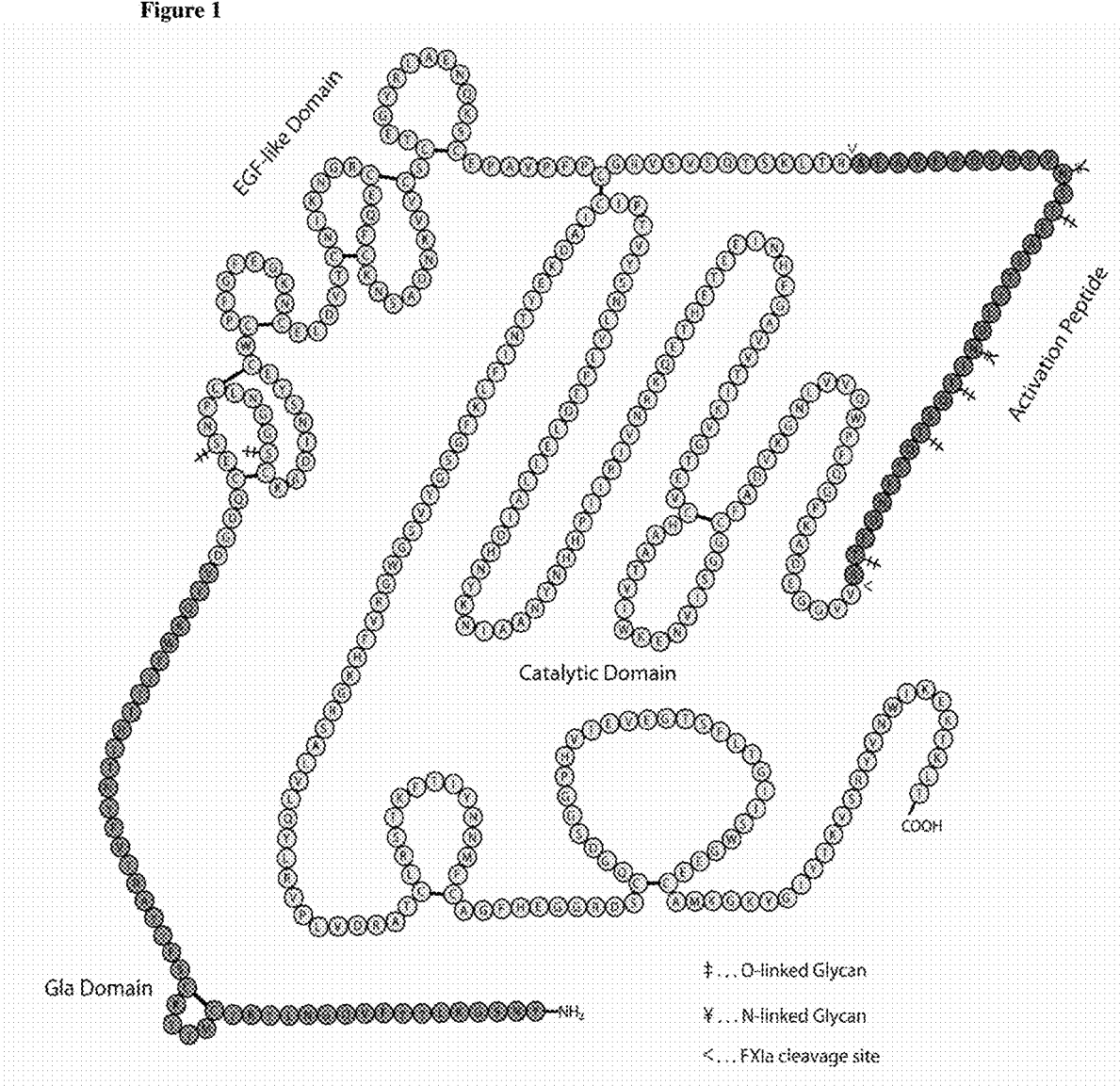
FIG. 1 shows the primary structure of coagulation Factor IX.

The pharmacological and immunological properties of therapeutic proteins can be improved by chemical modification and conjugation with polymeric compounds such as polyethylene glycol (PEG), branched PEG, polysialic acid (PSA), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly (1-hydroxymethylethylene hydroxymethylformal) (PHF), 2-methacryloyloxy-2'-ethyltrimethylammoniumphosphate (MPC). The properties of the resulting conjugates generally strongly depend on the structure and the size of the polymer. Thus, polymers with a defined and narrow size distribution are usually preferred in the art. Synthetic polymers like PEG can be manufactured easily with a narrow size distribution, while PSA can be purified in such a manner that results in a final PSA preparation with a narrow size distribution. In addition PEGylation reagents with defined polymer chains and narrow size distribution are on the market and commercially available for a reasonable price.

The addition of a soluble polymer, such as through polysialylation is one approach to improve the properties of a blood coagulation protein such as FIX, as well as other coagulation proteins (e.g., VWF, FVIIa (see, e.g., US 2008/0221032A1, incorporated herein by reference) and FVIII).

Blood Coagulation Proteins

As described herein, blood coagulation proteins including, but not limited to, Factor IX (FIX), Factor VIII (FVIII), Factor VIIa (FVIIa), Von Willebrand Factor (VWF), Factor FV (FV), Factor X (FX), Factor XI, Factor XII (FXII), thrombin (FII), protein C, protein S, tPA, PAI-1, tissue factor (TF) and ADAMTS 13 protease are contemplated by the invention. As used herein, the term "blood coagulation protein" refers to any Factor IX (FIX), Factor VIII (FVIII), Factor VIIa (FVIIa), Von Willebrand Factor (VWF), Factor FV (FV), Factor X (FX), Factor XII (FXII), thrombin (FII), protein C, protein S, tPA, PAI-1, tissue factor (TF) and ADAMTS 13 protease which exhibits biological activity that is associated with that particular native blood coagulation protein.

The blood coagulation cascade is divided into three distinct segments: the intrinsic, extrinsic, and common pathways (Schenone et al., Curr Opin Hematol. 2004; 11:272-7). The cascade involves a series of serine protease enzymes (zymogens) and protein cofactors. When required, an inactive zymogen precursor is converted into the active form, which consequently converts the next enzyme in the cascade.

The intrinsic pathway requires the clotting factors VIII, IX, X, XI, and XII. Initiation of the intrinsic pathway occurs when prekallikrein, high-molecular-weight kininogen, factor XI (FXI) and factor XII (FXII) are exposed to a negatively charged surface. Also required are calcium ions and phospholipids secreted from platelets.

The extrinsic pathway is initiated when the vascular lumen of blood vessels is damaged. The membrane glycoprotein tissue factor is exposed and then binds to circulating factor VII (FVII) and to small preexisting amounts of its activated form FVIIa. This binding facilitates full conversion of FVII to FVIIa and subsequently, in the presence of calcium and phospholipids, the conversion of factor IX (FIX) to factor IXa (FIXa) and factor X (FX) to factor Xa (FXa). The association of FVIIa with tissue factor enhances the proteolytic activity by bringing the binding sites of FVII for the substrate (FIX and FX) into closer proximity and by inducing a conformational change, which enhances the enzymatic activity of FVIIa.

The activation of FX is the common point of the two pathways. Along with phospholipid and calcium, factors Va (FVa) and Xa convert prothrombin to thrombin (prothrombinase complex), which then cleaves fibrinogen to form fibrin monomers. The monomers polymerize to form fibrin strands. Factor XIIIa (FXIIIa) covalently bonds these strands to one another to form a rigid mesh.

Conversion of FVII to FVIIa is also catalyzed by a number of proteases, including thrombin, FIXa, FXa, factor XIa (FXIa), and factor XIIa (FXIIa). For inhibition of the early phase of the cascade, tissue factor pathway inhibitor targets FVIIa/tissue factor/FXa product complex.

A. Polypeptides

In one aspect, the starting material of the present invention is a blood coagulation protein, which can be derived from human plasma, or produced by recombinant engineering techniques, as described in U.S. Pat. Nos. 4,757,006; 5,733,873; 5,198,349; 5,250,421; 5,919,766; and EP 306 968. As described herein, the term blood coagulation protein refers to any blood coagulation protein molecule which exhibits biological activity that is associated with the native blood coagulation protein. In one embodiment of the invention, the blood coagulation protein molecule is a full-length blood coagulation protein.

Blood coagulation protein molecules contemplated include full-length proteins, precursors of full length proteins, biologically active subunits or fragments of full length proteins, as well as biologically active derivatives and variants of any of these forms of blood coagulation proteins. Thus, blood coagulation protein include those that (1) have an amino acid sequence that has greater than about 60%, about 65%, about 70%, about 75%, about 80%, about 85%, about 90%, about 91%, about 92%, about 93%, about 94%, about 95%, about 96%, about 97%, about 98% or about 99% or greater amino acid sequence identity, over a region of at least about 25, about 50, about 100, about 200, about 300, about 400, or more amino acids, to a polypeptide encoded by a referenced nucleic acid or an amino acid sequence described herein; and/or (2) specifically bind to antibodies, e.g., polyclonal or monoclonal antibodies, generated against an immunogen comprising a referenced amino acid sequence as described herein, an immunogenic fragment thereof, and/or a conservatively modified variant thereof.

According to the present invention, the term "recombinant blood coagulation protein" includes any blood coagulation protein obtained via recombinant DNA technology. In certain embodiments, the term encompasses proteins as described herein.

As used herein, "endogenous blood coagulation protein" includes a blood coagulation protein which originates from the mammal intended to receive treatment. The term also includes blood coagulation protein transcribed from a transgene or any other foreign DNA present in said mammal. As used herein, "exogenous blood coagulation protein" includes a blood coagulation protein which does not originate from the mammal intended to receive treatment.

As used herein, "plasma-derived blood coagulation protein" or "plasmatic" includes all forms of the protein found in blood obtained from a mammal having the property participating in the coagulation pathway.

As used herein "biologically active derivative" or "biologically active variant" includes any derivative or variant of a molecule having substantially the same functional and/or biological properties of said molecule, such as binding properties, and/or the same structural basis, such as a peptidic backbone or a basic polymeric unit.

An "analog," "variant" or "derivative" is a compound substantially similar in structure and having the same biological activity, albeit in certain instances to a differing degree, to a naturally-occurring molecule. For example, a polypeptide variant refers to a polypeptide sharing substantially similar structure and having the same biological activity as a reference polypeptide. Variants or analogs differ in the composition of their amino acid sequences compared to the naturally-occurring polypeptide from which the analog is derived, based on one or more mutations involving (i) deletion of one or more amino acid residues at one or more termini of the polypeptide and/or one or more internal regions of the naturally-occurring polypeptide sequence (e.g., fragments), (ii) insertion or addition of one or more amino acids at one or more termini (typically an "addition" or "fusion") of the polypeptide and/or one or more internal regions (typically an "insertion") of the naturally-occurring polypeptide sequence or (iii) substitution of one or more amino acids for other amino acids in the naturally-occurring polypeptide sequence. By way of example, a "derivative" refers to a polypeptide sharing the same or substantially similar structure as a reference polypeptide that has been modified, e.g., chemically.

Variant or analog polypeptides include insertion variants, wherein one or more amino acid residues are added to a blood coagulation protein amino acid sequence of the invention. Insertions may be located at either or both termini of the protein, and/or may be positioned within internal regions of the blood coagulation protein amino acid sequence. Insertion variants, with additional residues at either or both termini, include for example, fusion proteins and proteins including amino acid tags or other amino acid labels. In one aspect, the blood coagulation protein molecule optionally contains an N-terminal Met, especially when the molecule is expressed recombinantly in a bacterial cell such as *E. coli*.

In deletion variants, one or more amino acid residues in a blood coagulation protein polypeptide as described herein are removed. Deletions can be effected at one or both termini of the blood coagulation protein polypeptide, and/or with removal of one or more residues within the blood coagulation protein amino acid sequence. Deletion variants, therefore, include fragments of a blood coagulation protein polypeptide sequence.

In substitution variants, one or more amino acid residues of a blood coagulation protein polypeptide are removed and replaced with alternative residues. In one aspect, the substitutions are conservative in nature and conservative substitutions of this type are well known in the art. Alternatively, the invention embraces substitutions that are also non-conservative. Exemplary conservative substitutions are described in Lehninger, [Biochemistry, 2nd Edition; Worth Publishers, Inc., New York (1975), pp. 71-77] and are set out immediately below.

| SIDE CHAIN CHARACTERISTIC | AMINO ACID |
|---|---|
| Non-polar (hydrophobic): | |
| A. Aliphatic | A L I V P |
| B. Aromatic | F W |
| C. Sulfur-containing | M |
| D. Borderline | G |
| Uncharged-polar: | |
| A. Hydroxyl | S T Y |
| B. Amides | N Q |
| C. Sulfhydryl | C |
| D. Borderline | G |
| Positively charged (basic) | K R H |
| Negatively charged (acidic) | D E |

Alternatively, exemplary conservative substitutions are set out immediately below.

Conservative Substitutions II

| ORIGINAL RESIDUE | EXEMPLARY SUBSTITUTION |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

B. Polynucleotides

Nucleic acids encoding a blood coagulation protein of the invention include, for example and without limitation, genes, pre-mRNAs, mRNAs, cDNAs, polymorphic variants, alleles, synthetic and naturally-occurring mutants.

Polynucleotides encoding a blood coagulation protein of the invention also include, without limitation, those that (1) specifically hybridize under stringent hybridization conditions to a nucleic acid encoding a referenced amino acid sequence as described herein, and conservatively modified variants thereof; (2) have a nucleic acid sequence that has greater than about 95%, about 96%, about 97%, about 98%, about 99%, or higher nucleotide sequence identity, over a region of at least about 25, about 50, about 100, about 150, about 200, about 250, about 500, about 1000, or more nucleotides (up to the full length sequence of 1218 nucleotides of the mature protein), to a reference nucleic acid sequence as described herein. Exemplary "stringent hybridization" conditions include hybridization at 42° C. in 50% formamide, 5×SSC, 20 mM Na.PO4, pH 6.8; and washing in 1×SSC at 55° C. for 30 minutes. It is understood that variation in these exemplary conditions can be made based on the length and GC nucleotide content of the sequences to be hybridized. Formulas standard in the art are appropriate for determining appropriate hybridization conditions. See Sambrook et al., Molecular Cloning: A Laboratory Manual (Second ed., Cold Spring Harbor Laboratory Press, 1989) §§ 9.47-9.51.

A "naturally-occurring" polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention can be recombinant molecules (e.g., heterologous and encoding the wild type sequence or a variant thereof, or non-naturally occurring).

In certain embodiments of the invention, the aforementioned polypeptides and polynucleotides are exemplified by the following blood coagulation proteins.

Factor VIIa

FVII (also known as stable factor or proconvertin) is a vitamin K-dependent serine protease glycoprotein with a pivotal role in hemostasis and coagulation (Eigenbrot, Curr Protein Pept Sci. 2002; 3:287-99).

FVII is synthesized in the liver and secreted as a single-chain glycoprotein of 48 kD. FVII shares with all vitamin K-dependent serine protease glycoproteins a similar protein domain structure consisting of an amino-terminal gamma-carboxyglutamic acid (Gla) domain with 9-12 residues responsible for the interaction of the protein with lipid membranes, a carboxy-terminal serine protease domain (catalytic domain), and two epidermal growth factor-like domains containing a calcium ion binding site that mediates interaction with tissue factor. Gamma-glutamyl carboxylase catalyzes carboxylation of Gla residues in the amino-terminal portion of the molecule. The carboxylase is dependent on a reduced form of vitamin K for its action, which is oxidized to the epoxide form. Vitamin K epoxide reductase is required to convert the epoxide form of vitamin K back to the reduced form.

The major proportion of FVII circulates in plasma in zymogen form, and activation of this form results in cleavage of the peptide bond between arginine 152 and isoleucine 153. The resulting activated FVIIa consists of a $NH_2$-derived light chain (20 kD) and a COOH terminal-derived heavy chain (30 kD) linked via a single disulfide bond (Cys 135 to Cys 262). The light chain contains the membrane-binding Gla domain, while the heavy chain contains the catalytic domain.

The plasma concentration of FVII determined by genetic and environmental factors is about 0.5 mg/mL (Pinotti et al., Blood. 2000; 95:3423-8). Different FVII genotypes can result in several-fold differences in mean FVII levels. Plasma FVII levels are elevated during pregnancy in healthy females and also increase with age and are higher in females and in persons with hypertriglyceridemia. FVII has the shortest half-life of all procoagulant factors (3-6 h). The mean plasma concentration of FVIIa is 3.6 ng/mL in healthy individuals and the circulating half-life of FVIIa is relatively long (2.5 h) compared with other coagulation factors.

Hereditary FVII deficiency is a rare autosomal recessive bleeding disorder with a prevalence estimated to be 1 case per 500,000 persons in the general population (Acharya et al., J Thromb Haemost. 2004; 2248-56). Acquired FVII deficiency from inhibitors is also very rare. Cases have also been reported with the deficiency occurring in association with drugs such as cephalosporins, penicillins, and oral anticoagulants. Furthermore, acquired FVII deficiency has been reported to occur spontaneously or with other conditions, such as myeloma, sepsis, aplastic anemia, with interleukin-2 and antithymocyte globulin therapy.

Reference polynucleotide and polypeptide sequences include, e.g., GenBank Accession Nos. J02933 for the genomic sequence, M13232 for the cDNA (Hagen et al. PNAS 1986; 83: 2412-6), and P08709 for the polypeptide sequence (references incorporated herein in their entireties). A variety of polymorphisms of FVII have been described, for example see Sabater-Lleal et al. (Hum Genet. 2006; 118:741-51) (reference incorporated herein in its entirety).

Factor IX

FIX is a vitamin K-dependent plasma protein that participates in the intrinsic pathway of blood coagulation by converting FX to its active form in the presence of calcium ions, phospholipids and FVIIIa. The predominant catalytic capability of FIX is as a serine protease with specificity for a particular arginine-isoleucine bond within FX. Activation of FIX occurs by FXIa which causes excision of the activation peptide from FIX to produce an activated FIX molecule comprising two chains held by one or more disulphide bonds. Defects in FIX are the cause of recessive X-linked hemophilia B.

Hemophilia A and B are inherited diseases characterized by deficiencies in FVIII and FIX polypeptides, respectively. The underlying cause of the deficiencies is frequently the result of mutations in FVIII and FIX genes, both of which are located on the X chromosome. Traditional therapy for hemophilias often involves intravenous administration of pooled plasma or semi-purified coagulation proteins from normal individuals. These preparations can be contaminated by pathogenic agents or viruses, such as infectious prions, HIV, parvovirus, hepatitis A, and hepatitis C. Hence, there is an urgent need for therapeutic agents that do not require the use of human serum.

The level of the decrease in FIX activity is directly proportional to the severity of hemophilia B. The current treatment of hemophilia B consists of the replacement of the missing protein by plasma-derived or recombinant FIX (so-called FIX substitution or replacement treatment or therapy).

Polynucleotide and polypeptide sequences of FIX can be found for example in the UniProtKB/Swiss-Prot Accession No. P00740, U.S. Pat. No. 6,531,298 and in FIG. 1.

Factor VIII

Coagulation factor VIII (FVIII) circulates in plasma at a very low concentration and is bound non-covalently to Von Willebrand factor (VWF). During hemostasis, FVIII is separated from VWF and acts as a cofactor for activated factor IX (FIXa)-mediated FX activation by enhancing the rate of activation in the presence of calcium and phospholipids or cellular membranes.

FVIII is synthesized as a single-chain precursor of approximately 270-330 kD with the domain structure A1-A2-B-A3-C1-C2. When purified from plasma (e.g., "plasma-derived" or "plasmatic"), FVIII is composed of a heavy chain (A1-A2-B) and a light chain (A3-C1-C2). The molecular mass of the light chain is 80 kD whereas, due to proteolysis within the B domain, the heavy chain is in the range of 90-220 kD.

FVIII is also synthesized as a recombinant protein for therapeutic use in bleeding disorders. Various in vitro assays have been devised to determine the potential efficacy of recombinant FVIII (rFVIII) as a therapeutic medicine. These assays mimic the in vivo effects of endogenous FVIII. In vitro thrombin treatment of FVIII results in a rapid increase and subsequent decrease in its procoagulant activity, as measured by in vitro assays. This activation and inactivation coincides with specific limited proteolysis both in the heavy and the light chains, which alter the availability of different binding epitopes in FVIII, e.g. allowing FVIII to dissociate from VWF and bind to a phospholipid surface or altering the binding ability to certain monoclonal antibodies.

The lack or dysfunction of FVIII is associated with the most frequent bleeding disorder, hemophilia A. The treatment of choice for the management of hemophilia A is replacement therapy with plasma derived or rFVIII concentrates. Patients with severe haemophilia A with FVIII levels below 1%, are generally on prophylactic therapy with the aim of keeping FVIII above 1% between doses. Taking into account the average half-lives of the various FVIII products in the circulation, this result can usually be achieved by giving FVIII two to three times a week.

Reference polynucleotide and polypeptide sequences include, e.g., UniProtKB/Swiss-Prot P00451 (FA8_HUMAN); Gitschier J et al., Characterization of the human Factor VIII gene, Nature, 312(5992): 326-30 (1984); Vehar G H et al., Structure of human Factor VIII, Nature, 312(5992):337-42 (1984); Thompson A R. Structure and Function of the Factor VIII gene and protein, Semin Thromb Hemost, 2003:29; 11-29 (2002).

Von Willebrand Factor

Von Willebrand factor (VWF) is a glycoprotein circulating in plasma as a series of multimers ranging in size from about 500 to 20,000 kD. Multimeric forms of VWF are composed of 250 kD polypeptide subunits linked together by disulfide bonds. VWF mediates initial platelet adhesion to the sub-endothelium of the damaged vessel wall. Only the larger multimers exhibit hemostatic activity. It is assumed that endothelial cells secrete large polymeric forms of VWF and those forms of VWF which have a low molecular weight (low molecular weight VWF) arise from proteolytic cleavage. The multimers having large molecular masses are stored in the Weibel-Pallade bodies of endothelial cells and liberated upon stimulation.

VWF is synthesized by endothelial cells and megakaryocytes as prepro-VWF that consists to a large extent of repeated domains. Upon cleavage of the signal peptide, pro-VWF dimerizes through disulfide linkages at its C-terminal region. The dimers serve as protomers for multimerization, which is governed by disulfide linkages between the free end termini. The assembly to multimers is followed by the proteolytic removal of the propeptide sequence (Leyte et al., Biochem. J. 274 (1991), 257-261).

The primary translation product predicted from the cloned cDNA of VWF is a 2813-residue precursor polypeptide (prepro-VWF). The prepro-VWF consists of a 22 amino acid signal peptide and a 741 amino acid propeptide, with the mature VWF comprising 2050 amino acids (Ruggeri Z. A., and Ware, J., FASEB J., 308-316 (1993).

Defects in VWF are causal to Von Willebrand disease (VWD), which is characterized by a more or less pronounced bleeding phenotype. VWD type 3 is the most severe form in which VWF is completely missing, and VWD type 1 relates to a quantitative loss of VWF and its phenotype can be very mild. VWD type 2 relates to qualitative defects of VWF and can be as severe as VWD type 3. VWD type 2 has many sub forms, some being associated with the loss or the decrease of high molecular weight multimers. Von Willebrand disease type 2a (VWD-2A) is characterized by a loss of both intermediate and large multimers. VWD-2B is characterized by a loss of highest-molecular-weight multimers. Other diseases and disorders related to VWF are known in the art.

The polynucleotide and amino acid sequences of prepro-VWF are available at GenBank Accession Nos. NM_000552 and NP_000543, respectively.

Other blood coagulation proteins according to the present invention are described in the art, e.g. Mann K G, Thromb Haemost, 1999; 82:165-74.

C. Production of Blood Coagulation Proteins

Production of a blood coagulation protein includes any method known in the art for (i) the production of recombinant DNA by genetic engineering, (ii) introducing recombinant DNA into prokaryotic or eukaryotic cells by, for example and without limitation, transfection, electroporation or microinjection, (iii) cultivating said transformed cells, (iv) expressing blood coagulation protein, e.g. constitutively or upon induction, and (v) isolating said blood coagulation protein, e.g. from the culture medium or by harvesting the transformed cells, in order to obtain purified blood coagulation protein.

In other aspects, the blood coagulation protein is produced by expression in a suitable prokaryotic or eukaryotic host system characterized by producing a pharmacologically acceptable blood coagulation protein molecule. Examples of eukaryotic cells are mammalian cells, such as CHO, COS, HEK 293, BHK, SK-Hep, and HepG2.

A wide variety of vectors are used for the preparation of the blood coagulation protein and are selected from eukaryotic and prokaryotic expression vectors. Examples of vectors for prokaryotic expression include plasmids such as, and without limitation, pRSET, pET, and pBAD, wherein the promoters used in prokaryotic expression vectors include one or more of, and without limitation, lac, trc, trp, recA, or araBAD. Examples of vectors for eukaryotic expression include: (i) for expression in yeast, vectors such as, and without limitation, pAO, pPIC, pYES, or pMET, using promoters such as, and without limitation, AOX1, GAP, GAL1, or AUG1; (ii) for expression in insect cells, vectors such as and without limitation, pMT, pAc5, pIB, pMIB, or pBAC, using promoters such as and without limitation PH, p10, MT, Ac5, OpIE2, gp64, or polh, and (iii) for expression in mammalian cells, vectors such as and without limitation pSVL, pCMV, pRc/RSV, pcDNA3, or pBPV, and vectors derived from, in one aspect, viral systems such as and without limitation vaccinia virus, adeno-associated viruses, herpes viruses, or retroviruses, using promoters such as and without limitation CMV, SV40, EF-1, UbC, RSV, ADV, BPV, and β-actin.

D. Administration

In one embodiment a conjugated blood coagulation protein of the present invention may be administered by injection, such as intravenous, intramuscular, or intraperitoneal injection.

To administer compositions comprising a conjugated blood coagulation protein of the present invention to human or test animals, in one aspect, the compositions comprise one or more pharmaceutically acceptable carriers. The terms "pharmaceutically" or "pharmacologically acceptable" refer to molecular entities and compositions that are stable, inhibit protein degradation such as aggregation and cleavage products, and in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like, including those agents disclosed above.

As used herein, "effective amount" includes a dose suitable for treating a mammal having a bleeding disorder as described herein.

The compositions may be administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramuscular, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

Single or multiple administrations of the compositions can be carried out with the dose levels and pattern being selected by the treating physician. For the prevention or treatment of disease, the appropriate dosage will depend on the type of disease to be treated, as described above, the severity and course of the disease, whether drug is administered for preventive or therapeutic purposes, previous therapy, the patient's clinical history and response to the drug, and the discretion of the attending physician.

The present invention also relates to a pharmaceutical composition comprising an effective amount of a conjugated blood coagulation protein as defined herein. The pharmaceutical composition may further comprise a pharmaceutically acceptable carrier, diluent, salt, buffer, or excipient. The pharmaceutical composition can be used for treating the above-defined bleeding disorders. The pharmaceutical composition of the invention may be a solution or a lyophilized product. Solutions of the pharmaceutical composition may be subjected to any suitable lyophilization process.

As an additional aspect, the invention includes kits which comprise a composition of the invention packaged in a manner which facilitates its use for administration to subjects. In one embodiment, such a kit includes a compound or composition described herein (e.g., a composition comprising a conjugated blood coagulation protein), packaged in a container such as a sealed bottle or vessel, with a label affixed to the container or included in the package that describes use of the compound or composition in practicing the method. In one embodiment, the kit contains a first container having a composition comprising a conjugated blood coagulation protein and a second container having a physiologically acceptable reconstitution solution for the composition in the first container. In one aspect, the compound or composition is packaged in a unit dosage form. The kit may further include a device suitable for administering the composition according to a specific route of administration. Preferably, the kit contains a label that describes use of the therapeutic protein or peptide composition.

Water Soluble Polymers

In one aspect, a blood coagulation protein derivative (i.e., a conjugated blood coagulation protein) molecule provided is bound to a water-soluble polymer including, but not limited to, polyethylene glycol (PEG), branched PEG, polysialic acid (PSA), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG) polyoxazoline, poly acryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), 2-methacryloyloxy-2'-ethyltrimethylammoniumphosphate (MPC). In one embodiment of the invention, the water soluble polymer is consisting of sialic acid molecule having a molecular weight range of 350 to 120,000, 500 to 100,000, 1000 to 80,000, 1500 to 60,000, 2,000 to 45,000 Da, 3,000 to 35,000 Da, and 5,000 to 25,000 Da. The coupling of the water soluble polymer can be carried out by direct coupling to the protein or via linker molecules. One example of a chemical linker is MBPH (4-[4-N-Maleimidophenyl]butyric acid hydrazide) containing a carbohydrate-selective hydrazide and a sulfhydryl-reactive maleimide group (Chamow et al., J Biol Chem 1992; 267:15916-22). Other exemplary and preferred linkers are described below.

In one embodiment, the derivative retains the full functional activity of native therapeutic blood coagulation protein products, and provides an extended half-life in vivo, as compared to native therapeutic blood coagulation protein products. In another embodiment, the derivative retains at least 20, 21, 22, 23, 24, 25, 26, 27, 28, 29, 30, 31, 32, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, or 150 percent (%) biological activity relative to native blood coagulation protein. In a related aspect, the biological activities of the derivative and native blood coagulation protein are determined by the ratios of chromogenic activity to blood coagulation factor antigen value (blood coagulation factor:Chr:blood coagulation factor:Ag). In still another embodiment of the invention, the half-life of the construct is decreased or increased 0.5, 0.6, 0.7, 0.8, 0.9, 1.0, 1.1, 1.2, 1.3, 1.4, 1.5, 2, 3, 4, 5, 6, 7, 8, 9, or 10-fold relative to the in vivo half-life of native blood coagulation protein.

A. Sialic Acid and PSA

As used herein, "sialic acid moieties" includes sialic acid monomers or polymers ("polysaccharides") which are soluble in an aqueous solution or suspension and have little or no negative impact, such as side effects, to mammals upon administration of the PSA-blood coagulation protein conjugate in a pharmaceutically effective amount. The polymers are characterized, in one aspect, as having 1, 2, 3, 4, 5, 10, 20, 30, 40, 50, 60, 70, 80, 90, 100, 200, 300, 400, or 500 sialic acid units. In certain aspects, different sialic acid units are combined in a chain.

In one embodiment of the invention, the sialic acid portion of the polysaccharide compound is highly hydrophilic, and in another embodiment the entire compound is highly hydrophilic. Hydrophilicity is conferred primarily by the pendant carboxyl groups of the sialic acid units, as well as the hydroxyl groups. The saccharide unit may contain other functional groups, such as, amine, hydroxyl or sulphate groups, or combinations thereof. These groups may be present on naturally-occurring saccharide compounds, or introduced into derivative polysaccharide compounds.

The naturally occurring polymer PSA is available as a polydisperse preparation showing a broad size distribution (e.g. Sigma C-5762) and high polydispersity (PD). Because the polysaccharides are usually produced in bacteria carrying the inherent risk of copurifying endotoxins, the purification of long sialic acid polymer chains may raise the probability of increased endotoxin content. Short PSA molecules with 1-4 sialic acid units can also be synthetically prepared (Kang S H et al., Chem Commun. 2000; 227-8; Ress D K and Linhardt R J, Current Organic Synthesis. 2004; 1:31-46), thus minimizing the risk of high endotoxin levels. However PSA preparations with a narrow size distribution and low polydispersity, which are also endotoxin-free, can now be manufactured. Polysaccharide compounds of particular use for the invention are, in one aspect, those produced by bacteria. Some of these naturally-occurring polysaccharides are known as glycolipids. In one embodiment, the polysaccharide compounds are substantially free of terminal galactose units.

B. Polyethylene Glycol (PEG) and Pegylation

In certain aspects, blood coagulation factor, e.g., FVIII, FVIIa, FIX, or other blood coagulation factor molecules are conjugated to a water soluble polymer by any of a variety of chemical methods (Roberts J M et al., Advan Drug Delivery Rev 2002; 54:459-76). For example, in one embodiment FVIII, FVIIa, or FIX is modified by the conjugation of PEG to free amino groups of the protein using N-hydroxysuccinimide (NHS) esters. In another embodiment the water soluble polymer, for example PEG, is coupled to free SH groups using maleimide chemistry or the coupling of PEG hydrazides or PEG amines to carbohydrate moieties of the FVIII, FVIIa, or FIX after prior oxidation.

The conjugation is in one aspect performed by direct coupling (or coupling via linker systems) of the water soluble polymer to blood coagulation factor, e.g., FVIII, FVIIa, or FIX, under formation of stable bonds. In addition degradable, releasable or hydrolysable linker systems are used in certain aspects the present invention (Tsubery et al. J Biol Chem 2004; 279:38118-24/Greenwald et al., J Med Chem 1999; 42:3657-67/Zhao et al., Bioconj Chem 2006; 17:341-51/WO2006/138572A2/U.S. Pat. No. 7,259,224B2/ U.S. Pat. No. 7,060,259B2).

In one embodiment of the invention, a blood coagulation factor, e.g., FVIII, FVIIa, or FIX, is modified via lysine residues by use of polyethylene glycol derivatives containing an active N-hydroxysuccinimide ester (NHS) such as succinimidyl succinate, succinimidyl glutarate or succinimidyl propionate. These derivatives react with the lysine residues of FVIII, FVIIa, or FIX under mild conditions by forming a stable amide bond. In one embodiment of the invention, the chain length of the PEG derivative is 5,000 Da. Other PEG derivatives with chain lengths of 500 to 2,000 Da, 2,000 to 5,000 Da, greater than 5,000 up to 10,000 Da or greater than 10,000 up to 20,000 Da, or greater than 20,000 up to 150,000 Da are used in various embodiments, including linear and branched structures.

Alternative methods for the PEGylation of amino groups are, without limitation, the chemical conjugation with PEG carbonates by forming urethane bonds, or the reaction with aldehydes or ketones by reductive amination forming secondary amide bonds.

In one embodiment of the present invention a blood coagulation factor, e.g., FVIII, FVIIa, FIX, or other blood coagulation factor, molecule is chemically modified using PEG derivatives that are commercially available. These PEG derivatives in alternative aspects have a linear or branched structures. Examples of PEG-derivatives containing NHS groups are listed below.

The following PEG derivatives are non-limiting examples of those commercially available from Nektar Therapeutics (Huntsville, Ala.; see www.nektar.com/PEG reagent catalog; Nektar Advanced PEGylation, price list 2005-2006):

mPEG-Succinimidyl propionate (mPEG-SPA)

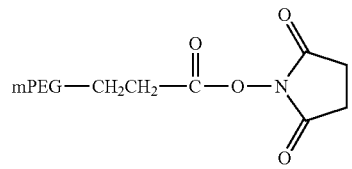

mPEG-Succinimidyl α-methylbutanoate (mPEG-SMB)

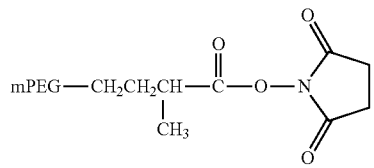

mPEG-CM-HBA-NHS  (CM=carboxymethyl; HBA=Hydroxy butyric acid)

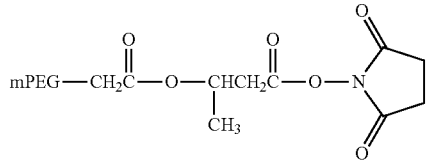

Structure of a Branched PEG-derivative (Nektar Therapeutics):
Branched PEG N-Hydroxysuccinimide (mPEG2-NHS)

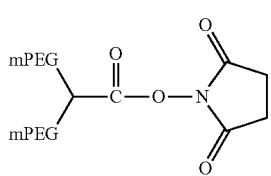

This reagent with branched structure is described in more detail by Kozlowski et al. (BioDrugs 2001; 5:419-29).

Other non-limiting examples of PEG derivatives are commercially available from NOF Corporation (Tokyo, Japan; see website: nof.co.jp/3nglish: Catalogue 2005)

General Structure of Linear PEG-Derivatives (NOF Corp.)

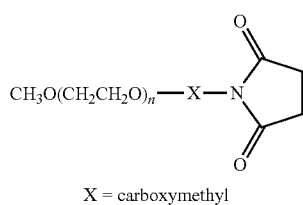

X = carboxymethyl

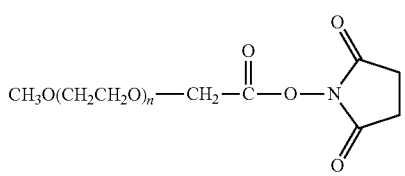

X = carboxypentyl

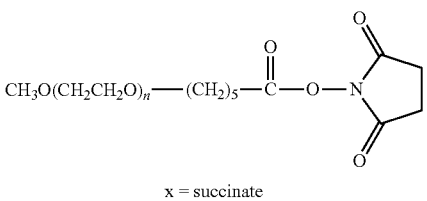

x = succinate

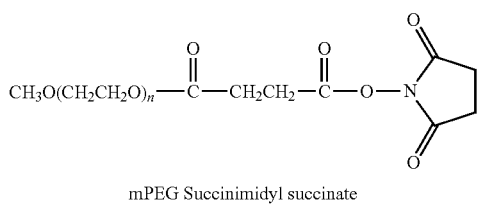

mPEG Succinimidyl succinate
x = glutarate

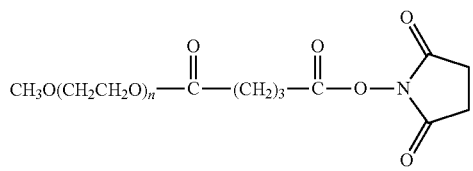

mPEG Succinimidyl glutarate

Structures of Branched PEG-derivatives (NOF Corp.): 2,3-Bis(methylpolyoxyethylene-oxy)-1-(1,5-dioxo-5-succinimidyloxy, pentyloxy)propane

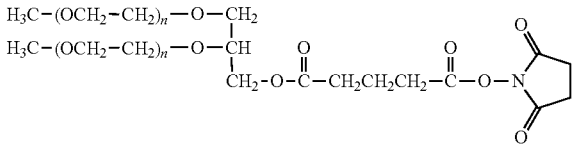

2,3-Bis(methylpolyoxyethylene-oxy)-1-(succinimidyl carboxypentyloxy)propane

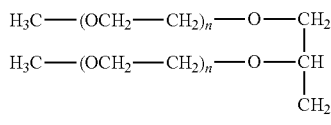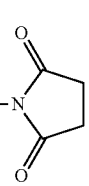

These propane derivatives show a glycerol backbone with a 1,2 substitution pattern. In the present invention branched PEG derivatives based on glycerol structures with 1,3 substitution or other branched structures described in US2003/0143596A1 are also contemplated.

PEG derivatives with degradable (for example, hydrolysable linkers) as described by Tsubery et al. (J Biol Chem 2004; 279:38118-24) and Shechter et al. (WO04089280A3) are also contemplated.

Surprisingly, the PEGylated FVIII, FVIIa, FIX, or other blood coagulation factor of this invention exhibits functional activity, combined with an extended half-life in vivo. In addition the PEGylated rFVIII, FVIIa, FIX, or other blood coagulation factor seems to be more resistant against thrombin inactivation.

C. Methods of Attachment

A blood coagulation protein may be covalently linked to the polysaccharide compounds by any of various techniques known to those of skill in the art. In various aspects of the invention, sialic acid moieties are bound to a blood coagulation protein, e.g., FIX, FVIII, FVIIa or VWF, for example by the method described in U.S. Pat. No. 4,356,170, which is herein incorporated by reference.

Other techniques for coupling PSA to polypeptides are also known and contemplated by the invention. For example, US Publication No. 2007/0282096 describes conjugating an amine or hydrazide derivative of, e.g., PSA, to proteins. In addition, US Publication No. 2007/0191597 describes PSA derivatives containing an aldehyde group for reaction with substrates (e.g., proteins) at the reducing end. These references are incorporated by reference in their entireties.

Various methods are disclosed at column 7, line 15, through column 8, line 5 of U.S. Pat. No. 5,846,951 (incorporated by reference in its entirety). Exemplary techniques include linkage through a peptide bond between a carboxyl group on one of either the blood coagulation protein or polysaccharide and an amine group of the blood coagulation protein or polysaccharide, or an ester linkage between a carboxyl group of the blood coagulation protein or polysaccharide and a hydroxyl group of the blood coagulation protein or polysaccharide. Another linkage by which the blood coagulation protein is covalently bonded to the polysaccharide compound is via a Schiff base, between a free amino group on the blood coagulation protein being reacted with an aldehyde group formed at the non-reducing end of the polysaccharide by periodate oxidation (Jennings H J and Lugowski C, J Immunol. 1981; 127:1011-8; Fernandes A I and Gregoriadis G, Biochim Biophys Acta. 1997; 1341; 26-34). The generated Schiff base is in one aspect stabilized by specific reduction with NaCNBH3 to form a secondary amine. An alternative approach is the generation of terminal free amino groups in the PSA by reductive amination with NH4Cl after prior oxidation. Bifunctional reagents can be used for linking two amino or two hydroxyl groups. For example, PSA containing an amino group is coupled to amino groups of the protein with reagents like BS3 (Bis(sulfosuccinimidyl)suberate/Pierce, Rockford, Ill.). In addition heterobifunctional cross linking reagents like Sulfo-EMCS (N-ε-Maleimidocaproyloxy) sulfosuccinimide ester/Pierce) is used for instance to link amine and thiol groups.

In another approach, a PSA hydrazide is prepared and coupled to the carbohydrate moiety of the protein after prior oxidation and generation of aldehyde functions.

As described above, a free amine group of the therapeutic protein reacts with the 1-carboxyl group of the sialic acid residue to form a peptidyl bond or an ester linkage is formed between the 1-carboxylic acid group and a hydroxyl or other suitable active group on a blood coagulation protein. Alternatively, a carboxyl group forms a peptide linkage with deacetylated 5-amino group, or an aldehyde group of a molecule of a blood coagulation protein forms a Schiff base with the N-deacetylated 5-amino group of a sialic acid residue.

Alternatively, the polysaccharide compound is associated in a non-covalent manner with a blood coagulation protein. For example, the polysaccharide compound and the pharmaceutically active compound are in one aspect linked via hydrophobic interactions. Other non-covalent associations include electrostatic interactions, with oppositely charged ions attracting each other.

In various embodiments, the blood coagulation protein is linked to or associated with the polysaccharide compound in stoichiometric amounts (e.g., 1:1, 1:2, 1:3, 1:4, 1:5, 1:6, 1:7, 1:7, 1:8, 1:9, or 1:10, etc.). In various embodiments, 1-6, 7-12 or 13-20 polysaccharides are linked to the blood coagulation protein. In still other embodiments, 1, 2, 3, 4, 5, 6, 7, 8, 9, 10, 11, 12, 13, 14, 15, 16, 17, 18, 19, 20 or more polysaccharides are linked to the blood coagulation protein.

In various embodiments, the blood coagulation protein is modified to introduce glycosylation sites (i.e., sites other than the native glycosylation sites). Such modification may be accomplished using standard molecular biological techniques known in the art. Moreover, the blood coagulation protein, prior to conjugation to a water soluble polymer via one or more carbohydrate moieties, may be glycosylated in vivo or in vitro. These glycosylated sites can serve as targets for conjugation of the proteins with water soluble polymers (US Patent Application No. 20090028822, US Patent Application No. 2009/0093399, US Patent Application No. 2009/0081188, US Patent Application No. 2007/0254836, US Patent Application No. 2006/0111279, and DeFrees S. et al., Glycobiology, 2006, 16, 9, 833-43).

D. Aminooxy Linkage

In one embodiment of the invention, the reaction of hydroxylamine or hydroxylamine derivatives with aldehydes (e.g., on a carbohydrate moiety following oxidation by sodium periodate) to form an oxime group is applied to the preparation of conjugates of blood coagulation protein. For example, a glycoprotein (e.g., a blood coagulation protein according to the present invention) is first oxidized with a oxidizing agent such as sodium periodate ($NaIO_4$) (Rothfus J A et Smith E L., J Biol Chem 1963, 238, 1402-10; and Van Lenten L and Ashwell G., J Biol Chem 1971, 246, 1889-94). The periodate oxidation of glycoproteins is based on the classical Malaprade reaction described in 1928, the oxidation of vicinal diols with periodate to form an active aldehyde group (Malaprade L., Analytical application, Bull Soc Chim France, 1928, 43, 683-96). Additional examples for such an oxidizing agent are lead tetraacetate ($Pb(OAc)_4$), manganese acetate ($MnO(Ac)_3$), cobalt acetate ($Co(OAc)_2$), thallium acetate (TlOAc), cerium sulfate ($Ce(SO_4)_2$) (U.S. Pat. No. 4,367,309) or potassium perruthenate ($KRuO_4$) (Marko et al., J Am Chem Soc 1997, 119, 12661-2) By "oxidizing agent" a mild oxidizing compound which is capable of oxidizing vicinal diols in carbohydrates, thereby generating active aldehyde groups under physiological reaction conditions is meant.

The second step is the coupling of the polymer containing an aminooxy group to the oxidized carbohydrate moiety to form an oxime linkage. In one embodiment of the invention, this step can be carried out in the presence of catalytic amounts of the nucleophilic catalyst aniline or aniline derivatives (Dirksen A et Dawson P E, Bioconjugate Chem.

Figure 2:
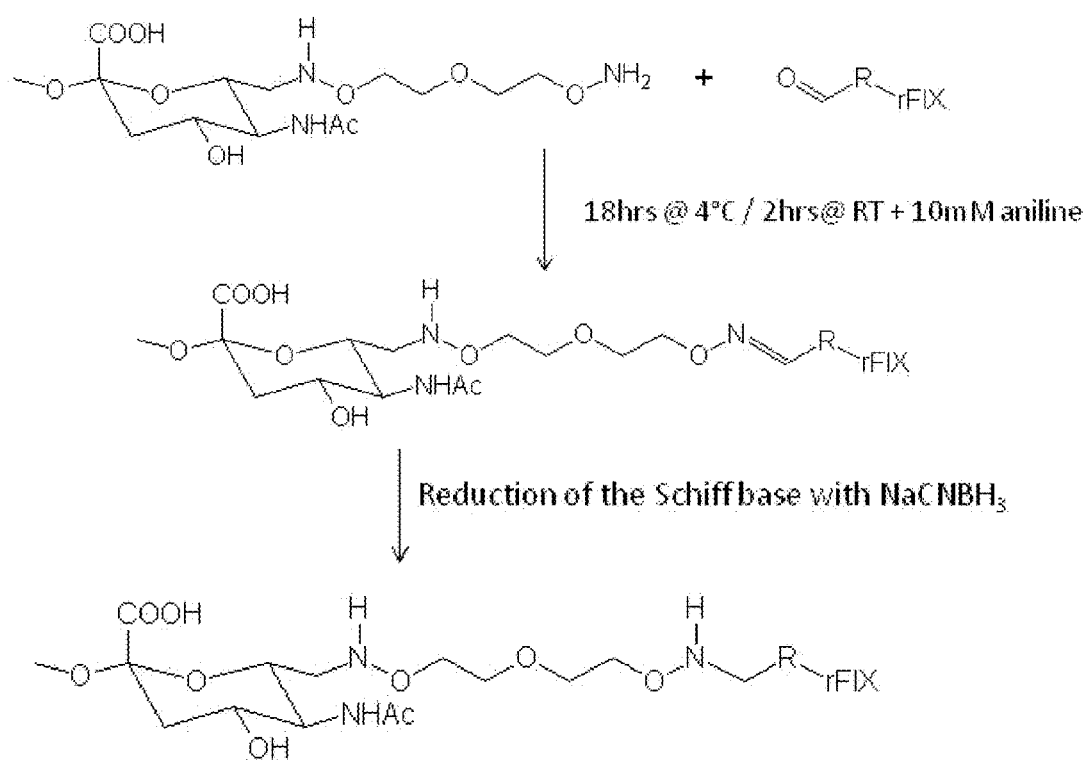
FIG. 2 shows the coupling of oxidized rFIX to aminooxy-PSA.

2008; Zeng Y et al., Nature Methods 2009; 6:207-9). The aniline catalysis dramatically accelerates the oxime ligation allowing the use of very low concentrations of the reagents. In another embodiment of the invention the oxime linkage is stabilized by reduction with NaCNBH3 to form an alkoxyamine linkage (FIG. 2).

In one embodiment of the invention, the reaction steps to conjugate a water soluble polymer to a blood coagulation protein are carried out separately and sequentially (i.e., starting materials (e.g., blood coagulation protein, water soluble polymer, etc), reagents (e.g., oxidizing agents, aniline, etc) and reaction products (e.g., oxidized carbohydrate on a blood coagulation protein, activated aminooxy water soluble polymer, etc) are separated between individual reaction steps).

Additional information on aminooxy technology can be found in the following references, each of which is incorporated in their entireties: EP 1681303A1 (HASylated erythropoietin); WO 2005/014024 (conjugates of a polymer and a protein linked by an oxime linking group); WO96/40662 (aminooxy-containing linker compounds and their application in conjugates); WO 2008/025856 (Modified proteins); Peri F et al., Tetrahedron 1998, 54, 12269-78; Kubler-Kielb J et. Pozsgay V., J Org Chem 2005, 70, 6887-90; Lees A et al., Vaccine 2006, 24(6), 716-29; and Heredia K L et al., Macromoecules 2007, 40(14), 4772-9.

In various embodiments of the invention, the water soluble polymer which is linked according to the aminooxy technology described herein to an oxidized carbohydrate moiety of a blood coagulation protein (e.g., FVIII, FVIIa, or FIX) include, but are not limited to polyethylene glycol (PEG), branched PEG, polysialic acid (PSA), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG) polyoxazoline, poly acryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), 2-methacryloyloxy-2'-ethyltrimethylammoniumphosphate (MPC).

The following examples are not intended to be limiting but only exemplary of specific embodiments of the invention.

Examples

Example 1

Preparation of the Homobifunctional Linker NH$_2$ [OCH$_2$CH$_2$]$_2$ONH$_2$

The homobifunctional linker NH$_2$[OCH$_2$CH$_2$]$_2$ONH$_2$

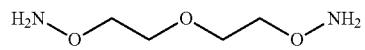

Figure 3:
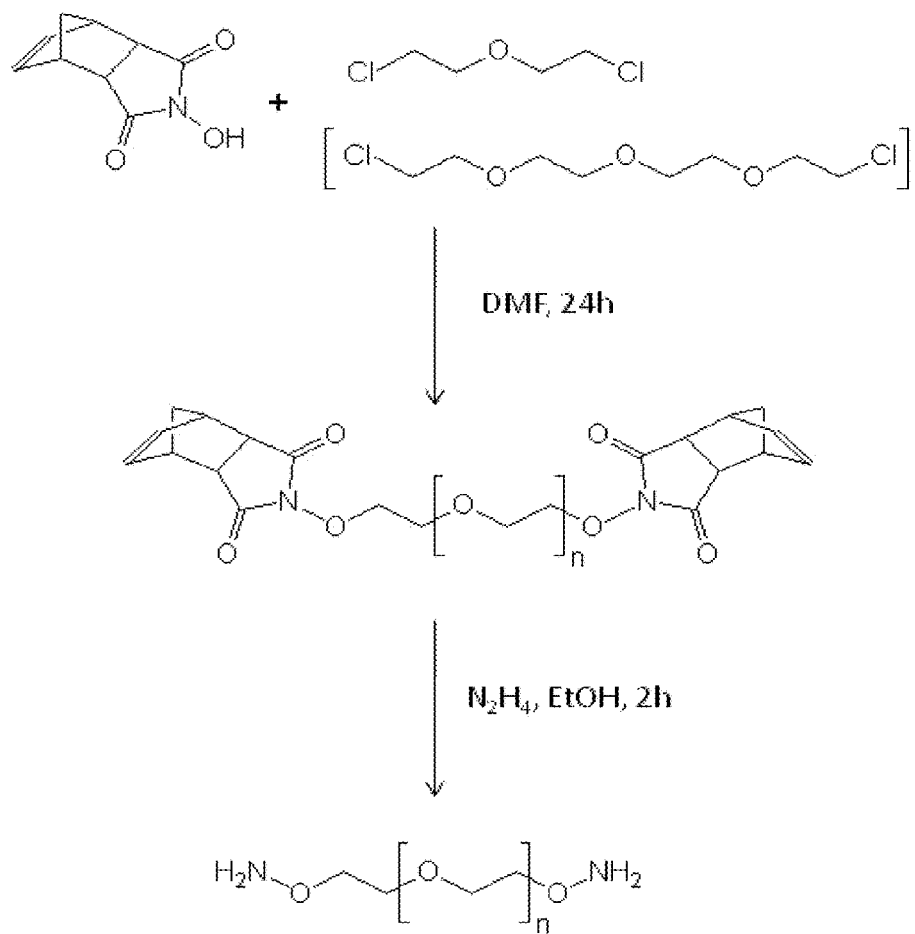
FIG. 3 shows the synthesis of the water soluble di-aminoxy linkers 3-oxa-pentane-1,5-dioxyamine and 3,6,9-trioxa-undecane-1,11-dioxyamine.

(3-oxa-pentane-1,5-dioxyamine) containing two active aminooxy groups was synthesized according to Boturyn et al. (Tetrahedron 1997; 53:5485-92) in a two step organic reaction employing a modified Gabriel-Synthesis of primary amines (FIG. 3). In the first step, one molecule of 2,2-chlorodiethylether was reacted with two molecules of Endo-N-hydroxy-5-norbornene-2,3-dicarboximide in dimethylformamide (DMF). The desired homobifunctional product was prepared from the resulting intermediate by hydrazinolysis in ethanol.

Example 2

Preparation of the Homobifunctional Linker NH$_2$ [OCH$_2$CH$_2$]$_4$ONH$_2$

The homobifunctional linker NH$_2$[OCH$_2$CH$_2$]$_4$ONH$_2$

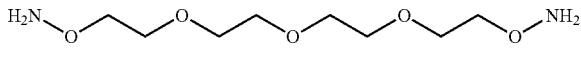 [SMILES: NOCCOCCOCCOCCON]

(3,6,9-trioxa-undecane-1,11-dioxyamine) containing two active aminooxy groups was synthesized according to Boturyn et al. (Tetrahedron 1997; 53:5485-92) in a two step organic reaction employing a modified Gabriel-Synthesis of primary amines (FIG. 3). In the first step one molecule of Bis-(2-(2-chlorethoxy)-ethyl)-ether was reacted with two molecules of Endo-N-hydroxy-5-norbornene-2,3-dicarboximide in DMF. The desired homobifunctional product was prepared from the resulting intermediate by hydrazinolysis in ethanol.

Example 3

Figure 4:
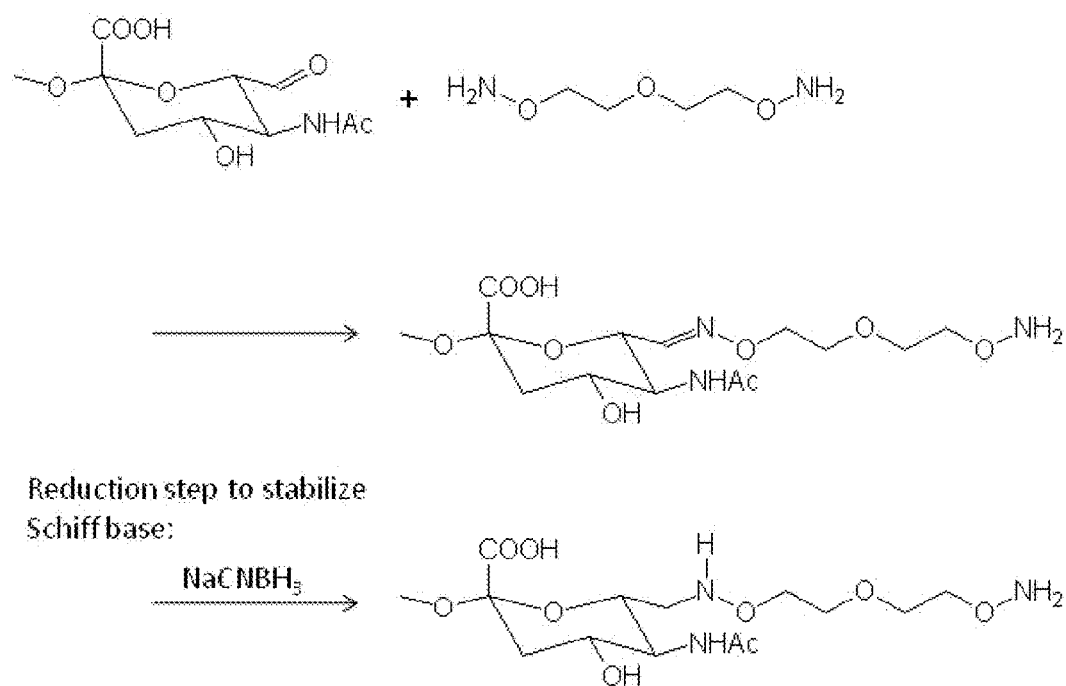
FIG. 4 shows the preparation of aminooxy-PSA.

Preparation of Aminooxy-PSA 500 mg of oxidized PSA (MW=18.8 kD) obtained from the Serum Institute of India (Pune, India) was dissolved in 8 ml 50 mM sodium acetate buffer, pH 5.5. Next, 100 mg 3-oxa-pentane-1,5-dioxyamine was added. After shaking for 2 hrs at room temperature, 44 mg sodium cyanoborohydride was added. After shaking for another 4 hrs at 4° C., the reaction mix was loaded into a Slide-A-Lyzer (Pierce, Rockford, Ill.) dialysis cassette (3.5 kD membrane, regenerated cellulose) and dialyzed against PBS pH 7.2 for 4 days. The product was frozen at −80° C. The preparation of the aminooxy-PSA according to this procedure is illustrated in FIG. 4.

Alternative Procedure for Preparation of Aminooxy PSA 1000 mg of oxidized PSA (MW=20 kD) obtained from the Serum Institute of India (Pune, India) was dissolved in 16 ml 50 mM phospate buffer pH 6.0. Then 170 mg 3-oxa-pentane-1,5-dioxyamine was given to the reaction mixture. After shaking for 2 hrs at RT 78.5 mg sodium cyanoborohydride was added and the reaction was performed for 18 hours over night. The reaction mixture was then subjected to a ultrafiltration/diafiltration procedure (UF/DF) using a membrane with a 5 kD cut-off made of regenerated cellulose (Millipore).

Example 4

Coupling of Aminooxy-PSA to rFIX and Purification of the Conjugate

To 12.6 mg rFIX, dissolved in 6.3 ml 50 mM sodium acetate buffer, pH 6.0, 2890 of an aqueous sodium periodate solution (10 mM) was added. The mixture was shaken in the dark for 1 h at 4° C. and quenched for 15 min at room temperature by the addition of 6.50 µl 1M glycerol. Low molecular weight contaminates were removed by ultrafiltration/diafiltration (UF/DF) employing Vivaspin (Sartorius, Goettingen, Germany) concentrators (30 kD membrane, regenerated cellulose). Next, 43 mg aminooxy-PSA was added to the UF/DF retentate and the mixture was shaken for 18 hrs at 4° C. The excess PSA reagent was removed by hydrophobic interaction chromatography (HIC). The conductivity of the cooled reaction mixture was raised to 180 mS/cm and loaded onto a 5 ml HiTrap Butyl FF (GE Healthcare, Fairfield, Conn.) HIC column (1.6×2.5 cm), pre-equilibrated with 50 mM HEPES, 3M sodium chloride, 6.7 mM calcium chloride, 0.01% Tween 80, pH 6.9. The conjugate was eluted within 2.4 column volumes (CV) with 50 mM HEPES, 6.7 mM calcium chloride, 0.005% Tween 80, pH 7.4 at a flow rate of 5 ml/min. The preparation was analytically characterized by measuring total protein (BCA) and FIX chromogenic activity. For the PSA-rFIX conjugate a specific activity of 80.2 IU/mg protein was determined (56.4% in comparison to native rFIX). The results are summarized in Table 1.

TABLE 1

| Item | BCA [mg/ml] | FIX:Chrom [IU/ml] | Specific Activity [IU FIX:Chrom/mg BCA] | Specific Activity [%] |
| --- | --- | --- | --- | --- |
| rFIX | 8.58 | 1221 | 142.3 | 100 |
| PSA-rFIX | 1.15 | 92.2 | 80.2 | 56.4 |

Figure 5:
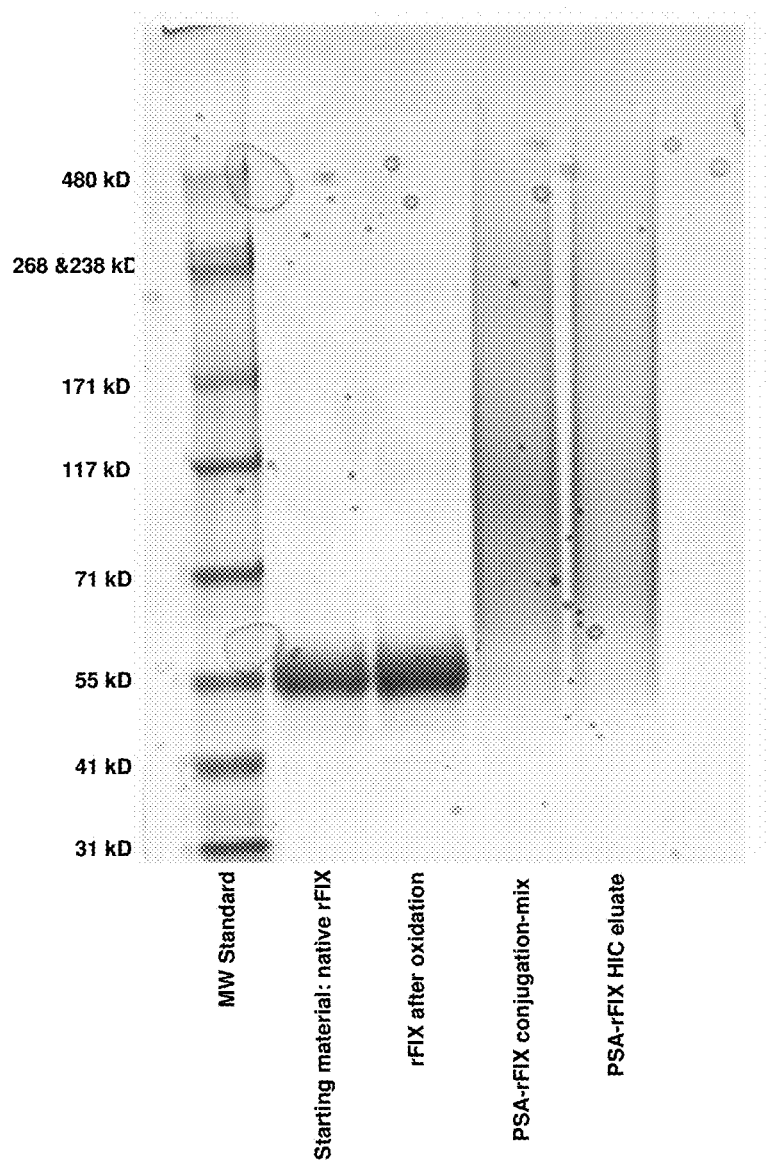
FIG. 5 shows the analytical characterization of the PSA-rFIX conjugate employing SDS-PAGE and Coomassie staining.
Figure 6:
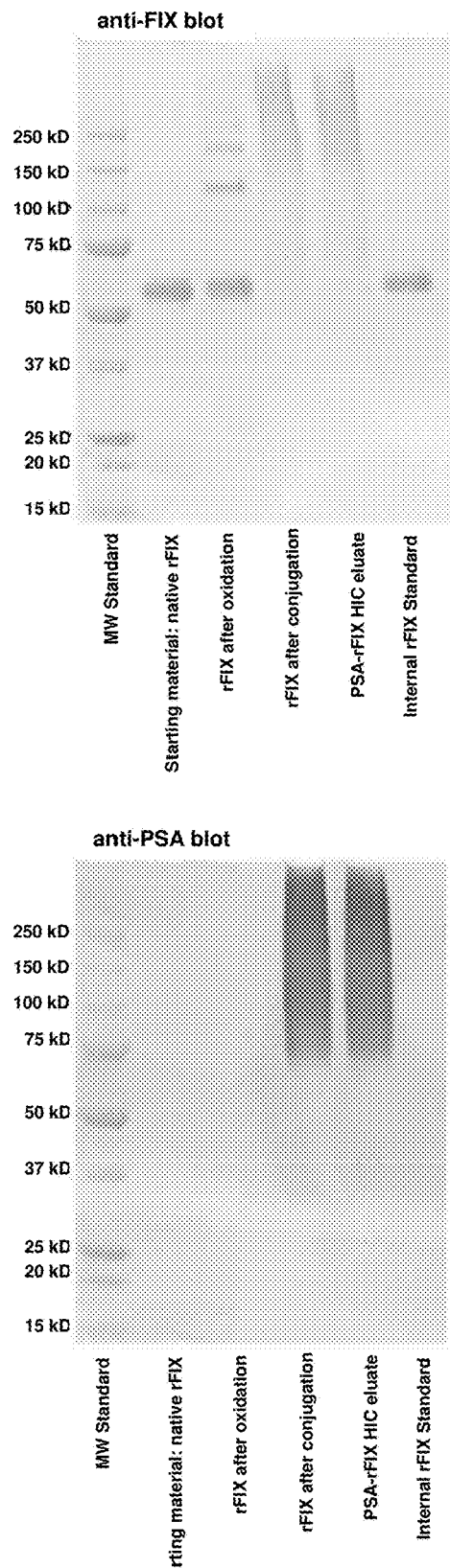
FIG. 6 shows the analytical characterization of the PSA-rFIX conjugate employing detection with anti-FIX and anti-PSA antibodies.

The analytical characterization of the PSA-rFIX conjugate by SDS-PAGE with Coomassie staining is illustrated in FIG. 5. An SDS-PAGE followed by Western blot employing anti-FIX and anti-PSA antibodies is shown in FIG. 6.

Example 5

Coupling of Aminooxy-PSA to rFIX in the Presence of Aniline as Nucleophilic Catalyst To 3.0 mg rFIX, dissolved in 1.4 ml 50 mM sodium acetate buffer, pH 6.0, 14.10 of an aqueous sodium periodate solution (10 mM) was added. The mixture was shaken in the dark for 1 h at 4° C. and quenched for 15 min at room temperature by the addition of 1.50 µl 1M glycerol. Low molecular weight contaminates were removed by means of size exclusion chromatography (SEC) employing PD-10 desalting columns (GE Healthcare, Fairfield, Conn.). 1.2 mg oxidized rFIX, dissolved in 1.33 ml 50 mM sodium acetate buffer, pH 6.0 was mixed with 70 µl of aniline (200 mM aqueous stock solution) and shaken for 45 min at room temperature. Next, 4.0 mg aminooxy-PSA was added and the mixture was shaken for 2 hrs at room temperature and another 16 hrs at 4° C. Samples were drawn after 1 h, after 2 hrs and at the end of the reaction after 18 hrs. Next, excess PSA reagent and free rFIX were removed by means of HIC. The conductivity of the cooled reaction mixture was raised to 180 mS/cm and loaded onto a 5 ml HiTrap Butyl FF (GE Healthcare, Fairfield, Conn.) HIC column (1.6×2.5 cm), pre-equilibrated with 50 mM HEPES, 3M sodium chloride, 6.7 mM calcium chloride, 0.01% Tween 80, pH 6.9. The conjugate was eluted with a linear gradient to 50 mM HEPES, 6.7 mM calcium chloride, 0.005% Tween 80, pH 7.4 in 20 CV with at a flow rate of 5 ml/min.

Example 6

Coupling of Aminooxy-PSA to rFIX and Reduction with NaCNBH$_3$

To 10.5 mg rFIX, dissolved in 5.25 ml 50 mM sodium acetate buffer, pH 6.0, 530 of an aqueous sodium periodate solution (10 mM) was added. The mixture was shaken in the dark for 1 h at 4° C. and quenched for 15 min at room temperature by the addition of 5.30 µl 1M glycerol. Low molecular weight contaminates were removed by means of UF/DF employing Vivaspin (Sartorius, Goettingen, Germany) concentrators (30 kD membrane, regenerated cellulose). Next, 35.9 mg aminooxy-PSA was added to the UF/DF retentate and the mixture was shaken for 2 hrs at room temperature. Then 530 of a aqueous sodium cyanoborohydride solution (5M) was added and the reaction was allowed to proceed for another 16 hrs. Then the excess PSA reagent was removed by means of HIC. The conductivity of the cooled reaction mixture was raised to 180 mS/cm and loaded onto a 5 ml HiTrap Butyl FF HIC (GE Healthcare, Fairfield, Conn.) column (1.6×2.5 cm), pre-equilibrated with 50 mM HEPES, 3M sodium chloride, 6.7 mM calcium chloride, 0.01% Tween 80, pH 6.9. The conjugate was eluted within 2.4 CV with 50 mM HEPES, 6.7 mM calcium chloride, 0.005% Tween 80, pH 7.4 at a flow rate of 5 ml/min.

Example 7

Coupling of Aminooxy-PSA (Linker: NH$_2$ [OCH$_2$CH$_2$]$_4$ONH$_2$) to rFIX and Purification of the Conjugate To 5.6 mg rFIX, dissolved in 2.8 ml 50 mM sodium acetate buffer, pH 6.0, 102 µl of an aqueous solution of sodium periodate (10 mM) was added. The mixture was shaken in the dark for 1 h at 4° C. and quenched for 15 min at room temperature by the addition of 2.9 µl of 1M glycerol. Low molecular weight contaminates were removed by means of UF/DF employing Vivaspin (Sartorius, Goettingen, Germany) concentrators (30 kD membrane, regenerated cellulose). Then 19 mg aminooxy-PSA was added to the UF/DF retentate and the mixture was shaken for 18 hrs at 4° C. The excess PSA reagent was removed by means of HIC. The conductivity of the cooled reaction mixture was raised to 180 mS/cm and loaded onto a 5 ml HiTrap Butyl FF (GE Healthcare, Fairfield, Conn.) HIC column (1.6×2.5 cm), pre-equilibrated with 50 mM HEPES, 3M sodium chloride, 6.7 mM calcium chloride, 0.01% Tween 80, pH 6.9. The conjugate was eluted within 2.4 CV with 50 mM HEPES, 6.7 mM calcium chloride, 0.005% Tween 80, pH 7.4 at a flow rate of 5 ml/min.

Example 8

Coupling of Aminooxy-PSA to rFVIII

To 11 mg rFVIII, dissolved in 11 ml Hepes buffer pH 6 (50 mM Hepes, 5 mM CaCl$_2$, 150 mM NaCl, 0.01% Tween) 57 µl 10 mM sodium periodate was added. The mixture was shaken in the dark for 30 min at 4° C. and quenched for 30 min at 4° C. by the addition of 107 µl of an aqueous 1M glycerol solution. Then 19.8 mg aminooxy-PSA (18.8 kD) was added and the mixture was shaken over night at 4° C. The ionic strength was increased by adding a buffer containing 8M ammonium acetate (8M ammonium acetate, 50 mM Hepes, 5 mM CaCl$_2$, 350 mM NaCl, 0.01% Tween 80, pH 6.9) to get a final concentration of 2.5M ammonium acetate. Next, the reaction mixture was loaded on a HiTrap Butyl FF (GE Healthcare, Fairfield, Conn.) column which was equilibrated with equilibration buffer (2.5M ammonium acetate, 50 mM Hepes, 5 mM CaCl$_2$, 350 mM NaCl, 0.01% Tween 80, pH 6.9). The product was eluted with elution buffer (50 mM Hepes, 5 mM CaCl₂, 0.01% Tween 80, pH 7.4), and the eluate was concentrated by centrifugal filtration using Vivaspin (Sartorius, Goettingen, Germany) devices with 30,000 MWCO.

Example 9

PK Studies in Hemophilic Mice

FIX-deficient mice were injected with either rFIX or PSA-rFIX (prepared according to Example 4) in formulation buffer (10 mM histidine, 260 mM glycine, 29 mM sucrose, 0.005% Tween 80, pH 6.8) in a volume dose of 10 ml/kg bodyweight. Groups of 6 mice were sacrificed 5 minutes, 3 hours, 9, 16, 24 and 48 hours after substance injection and blood was collected by heart puncture. Citrated plasma was prepared and stored frozen until analysis of FIX activity.

Figure 7:
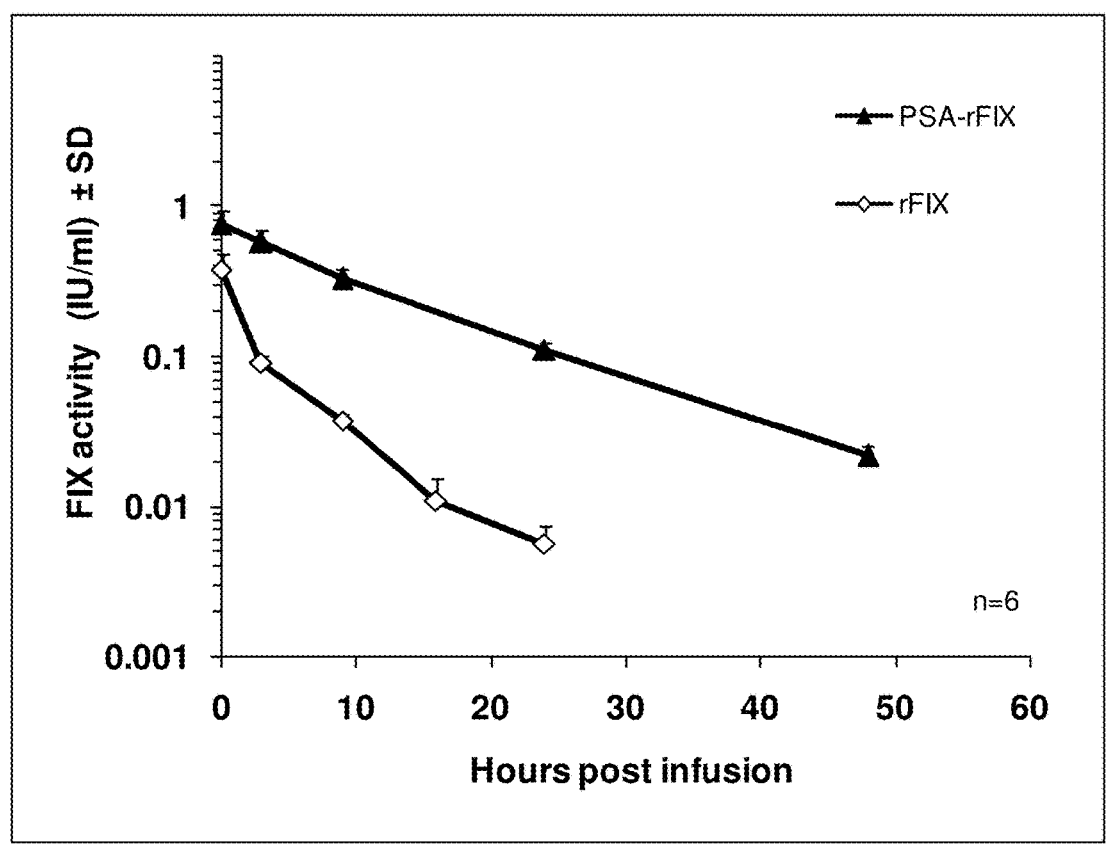
FIG. 7 shows activity of native rFIX and PSA-rFIX conjugate relative to time post infusions.

FIX activity was determined with a chromogenic FIX assay (Biophen FIX assay, Hyphen Biomed, Neuville-sur-Oise, France) and elimination curves were constructed (FIG. 7). Actual FIX activity doses were 123 IU FIX/kg for PSA-rFIX and 143 IU FIX/kg for rFIX. Pharmacokinetic parameters were calculated with program R (The R Foundation for Statistical Computing, 2008). In vivo recovery was 13% for rFIX and 29% for PSA-rFIX. Dose adjusted AUC for PSA-rFIX increased 6.4-fold relative to rFIX, terminal half life increased by a factor of 1.2 and MRT was 1.7-times longer for PSA-rFIX compared to rFIX (Table 2).

mide in DMF. The desired homobifunctional product was prepared from the resulting intermediate by hydrazinolysis in ethanol.

Example 12

Polysialylation of rFIX Employing a Maleimido/Aminooxy Linker System

A. Preparation of the Modification Reagent

An Aminooxy-PSA reagent is prepared by use of a maleimido/aminooxy linker system (Toyokuni et al., Bioconjugate Chem 2003; 14, 1253-9). PSA-SH (20 kD) containing a free terminal SH-group is prepared using a two step procedure: a) Preparation of PSA-NH₂ by reductive amination of oxidized PSA with NH₄Cl according to WO05016973A1 and b) introduction of a sulfhydryl group by reaction of the terminal primary amino group with 2-iminothiolane (Traut's reagent/Pierce, Rockford, Ill.) as described in U.S. Pat. No. 7,645,860. PSA-SH is coupled to the maleimido-group of the linker at pH 7.5 in PBS-buffer using a 10 fold molar excess of the linker and a PSA-SH concentration of 50 mg/ml. The reaction mixture is incubated for 2 hours under gentle shaking at room temperature. Then the excess linker reagent is removed and the aminooxy-PSA is buffer exchanged into oxidation buffer (50 mM sodium phosphate, pH 6.0) by diafiltration. The buffer

TABLE 2

| Item | In vivo recovery [%] | AUC [(IU/ml)/(IU/kg)] | Increase factor | Terminal HL [h] | Increase factor | MRT [h] | Increase factor |
|---|---|---|---|---|---|---|---|
| rFIX | 13 | 0.0100 | =1 | 8.0 | =1 | 7.3 | =1 |
| PSA-rFIX | 29 | 0.0650 | 6.4x | 9.6 | 1.2x | 12.3 | 1.7x |

Example 10

Polysialylation of Blood Coagulation Proteins

Polysialylation as described herein may be extended to other coagulation proteins. For example, in various aspects of the invention, the above polysialylation as described in Examples 5, 6 and 9 with aminooxy-PSA is repeated with coagulation proteins such as FVIII, FVIIa and VWF.

Example 11

Preparation of the Homobifunctional Linker NH₂[OCH₂CH₂]₆ONH₂

The homobifunctional linker NH₂[OCH₂CH₂]₆ONH₂ is exchanged 25 times employing a Pellicon XL5 kD regenerated cellulose membrane (Millipore, Billerica, Mass.).

B. Modification of rFIX after Prior Oxidation with NaIO₄ rFIX is oxidized in 50 mM sodium phosphate buffer, pH 6.0 employing 100 µM sodium periodate in the buffer. The mixture was shaken in the dark for 1 h at 4° C. and quenched for 15 min at room temperature by the addition of glycerol to a final concentration of 5 mM. Low molecular weight contaminates were removed by means of size exclusion chromatography (SEC) employing PD-10 desalting columns (GE Healthcare, Fairfield, Conn.). Oxidized rFIX is then spiked with aniline to obtain a final concentration of 10 mM and mixed with the aminooxy-PSA reagent to achieve a 5 fold molar excess of PSA. The reaction mixture was incubated for 2 hours under gentle shaking in the dark at room temperature.

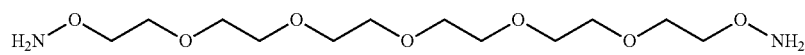 [SMILES: NOCCOCCOCCOCCOCCOCCON]

(3,6,9,12,15-penatoxa-heptadecane-1,17-dioxyamine) containing two active aminooxy groups was synthesized according to Boturyn et al. (Tetrahedron 1997; 53:5485-92) in a two step organic reaction employing a modified Gabriel-Synthesis of primary amines. In the first step one molecule of hexaethylene glycol dichloride was reacted with two molecules of Endo-N-hydroxy-5-norbornene-2,3-dicarboxi- C. Purification of the Conjugates The excess of PSA reagent and free rFIX is removed by means of HIC. The conductivity of the reaction mixture is raised to 180 mS/cm and loaded onto a column filled with 48 ml Butyl-Sepharose FF (GE Healthcare, Fairfield, Conn.) pre-equilibrated with 50 mM Hepes, 3 M sodium chloride, 6.7 mM calcium chloride, 0.01% Tween 80, pH 6.9. Subsequently the conjugate is eluted with a linear gradient of 60% elution buffer (50 mM Hepes, 6.7 mM calcium chloride, pH 7.4) in 40 CV. Finally the PSA-rFIX containing fractions are collected and subjected to UF/DF by use of a 30 kD membrane made of regenerated cellulose (Millipore). The preparation is analytically characterized by measuring total protein (BCA) and FIX chromogenic activity. For the PSA-rFIX conjugates prepared with both variants a specific activity of >50% in comparison to native rFIX is determined.

Example 13

Preparation of Aminooxy-PSA Reagent

An Aminooxy-PSA reagent was prepared according to Example 3. The final product was diafiltrated against buffer, pH 7.2 (50 mM Hepes) using a 5 kD membrane (regenerated cellulose, Millipore), frozen at −80° C. and lyophilized. After lyophilization the reagent was dissolved in the appropriate volume of water and used for preparation of PSA-protein conjugates via carbohydrate modification.

Example 14

Pharmacokinetics of Polysialylated rFVIII in a FVIII Deficient Knock Out Mouse Model A PSA-FVIII conjugate was prepared according Example 8. The conjugate showed a specific activity of 6237 IU/mg (FVIII activity determined by the chromogenic assay; total protein determined by the Bradford assay) and had a polysialylation degree of 6.7 (mole PSA per mole FVIII) as measured by the Resorcinol assay (Svennerholm L, Biochim Biophys Acta 1957; 24: 604-11).

Figure 8:
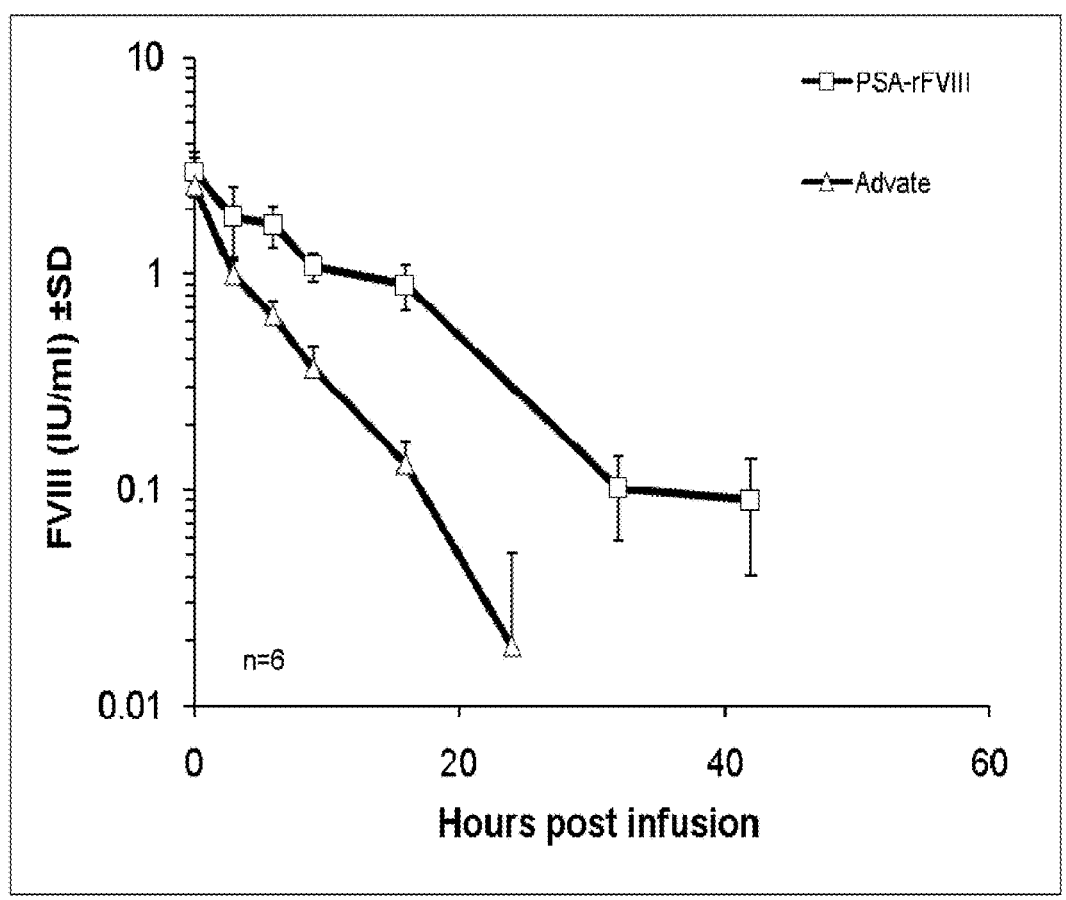
FIG. 8 shows PSA-rFVIII and Advate levels relative to time post infusion.

FVIII deficient mice described in detail by Bi et al. (Nat Genet 1995; 10:119-21) were used as a model of severe human hemophilia A. Groups of 6 mice received a bolus injection (200 IU FVIII/kg) via the tail vein with either PSA-rFVIII prepared according to Example 8 or native rFVIII (ADVATE, Baxter Healthcare Corporation) in a dose of 200 IU FVIII/kg bodyweight. Citrate plasma by heart puncture after anesthesia was prepared from the respective groups 5 minutes, 3, 6, 9, 16, 24, 32 and 42 hours after injection. FVIII activity levels were measured in plasma samples by use of the chromogenic assay. The results of this experiment are summarized in Table 3 and illustrated in FIG. 8. All calculations were performed with R version 2.10.1 (A language and environment for statistical computing. R Foundation for Statistical Computing, Vienna, Austria. website: R-project.org.). As a result the mean residence time (MRT) increased from 5.4 h (Advate control) to 11.1 h for the PSA-rFVIII conjugate.

TABLE 3

| Item | In vivo recovery IVR % | AUC 0-24 (IU/ml · h)/ IU/kg | Terminal half-life (h) | Mean residence time MRT (h) | Clearance CL (ml/h/kg) |
|---|---|---|---|---|---|
| PSA-rFVIII | 71 | 0.161 | 7.2 | 11.1 | 6.0 |
| rFVIII control (Advate) | 58 | 0.054 | 4.4 | 5.4 | 17.1 |

Example 15

Detailed Synthesis of the Aminooxy-PSA Reagent 3-oxa-pentane-1,5 dioxyamine was synthesized according to Botyryn et al (Tetrahedron 1997; 53:5485-92) in a two step organic synthesis as outlined in Example 1.

Step 1:
To a solution of Endo-N-hydroxy-5-norbonene-2,3-dicarboxiimide (59.0 g; 1.00 eq) in 700 ml anhydrous N,N-dimetylformamide anhydrous $K_2CO_3$ (45.51 g; 1.00 eq) and 2,2-dichlorodiethylether (15.84 ml; 0.41 eq) were added. The reaction mixture was stirred for 22 h at 50° C. The mixture was evaporated to dryness under reduced pressure. The residue was suspended in 2 L dichloromethane and extracted two times with saturated aqueous NaCl-solution (each 1 L). The Dichloromethane layer was dried over $Na_2SO_4$ and then evaporated to dryness under reduced pressure and dried in high vacuum to give 64.5 g of 3-oxapentane-1,5-dioxy-endo-2',3'-dicarboxydiimidenorbornene as a white-yellow solid (intermediate 1).

Step 2:
To a solution of intermediate 1 (64.25 g; 1.00 eq) in 800 ml anhydrous Ethanol, 31.0 ml Hydrazine hydrate (4.26 eq) were added. The reaction mixture was then refluxed for 2 hrs. The mixture was concentrated to the half of the starting volume by evaporating the solvent under reduced pressure. The occurring precipitate was filtered off. The remaining ethanol layer was evaporated to dryness under reduced pressure. The residue containing the crude product 3-oxa-pentane-1,5-dioxyamine was dried in vacuum to yield 46.3 g. The crude product was further purified by column chromatography (Silicagel 60; isocratic elution with Dichloromethane/Methanol mixture, 9+1) to yield 11.7 g of the pure final product 3-oxa-pentane-1,5-dioxyamine.

Example 16

Polysialylation of rFIX Using PSA Hydrazide rFIX is polysialylated by use of a PSA hydrazide reagent, which was prepared by reaction of oxidized PSA with adipic acid dihydrazide (ADH).

Step 1: Preparation of PSA Hydrazide 500 mg of oxidized PSA (MW=20 kD) obtained from the Serum Institute of India (Pune, India) was dissolved in 8 ml 50 mM sodium acetate buffer, pH 5.5. 100 mg adipic acid dihydrazide (ADH) was then added. The solution was gently shaken for 2 hrs. 44 mg sodium cyanoborohydride were then added. After the reaction was incubated for an additional 4 hrs at 4° C., the reaction mix was loaded into a Slide-A-Lyzer (Pierce, Rockford, Ill.) dialysis cassette (3.5 kD membrane, regenerated cellulose) and dialyzed against PBS pH 7.2 for 4 days. The product was frozen at −80° C.

Step 2: Reaction of PSA Hydrazide with rFIX and Purification of the Conjugate rFIX is polysialylated by use of a PSA hydrazide reagent as described in Step 1. rFIX (concentration 1 mg/ml) is oxidized with $NaIO_4$ (concentration: 80 µM) for 1 h at 4° C. in the dark under gentle shaking. The reaction is stopped by addition of glycerol and the oxidized FIX is subjected to UF/DF by use of a 30 kD membrane made of regenerated cellulose (Vivaspin). The oxidized rFIX is then polysialylated at pH 6.5 using a 200-fold molar excess of reagent and a protein concentration of 1 mg/ml. rFIX and the polysialyation reagent are incubated for 2 hours under gentle shaking in the dark at room temperature. Finally, the PSA-rFIX conjugate is purified by HIC. The conductivity of the reaction mixture is raised to 130 mS/cm by adding a buffer containing ammonium acetate (50 mM Hepes, 350 mM NaCl, 5 mM Calcium chloride, 8M ammonium acetate, 0.01% Tween 80, pH 6.9) and loaded onto a HiTrap Butyl FF column (5 ml, GE Healthcare, Fairfield, Conn.) pre-equilibrated with 50 mM Hepes, 2.5M ammonium acetate, 350 mM sodium chloride, 5 mM calcium chloride, 0.01% Tween 80, pH 6.9. Subsequently, the conjugate is eluted with 50 mM Hepes, 5 mM calcium chloride, 0.01% Tween 80, pH 7.4. Finally the PSA-rFIX containing fractions are collected and subjected to UF/DF by use of a 30 kD membrane made of regenerated cellulose (Vivaspin). For the PEG-rFIX conjugate, a specific activity of >50% in comparison to native rFIX is determined (chromogenic assay).

Example 17

Polysialylation of rFIX Using PSA Hydrazide in the Presence of Aniline as a Nucleophilic Catalyst 123 mg rFIX are dissolved in 60 ml phosphate buffer (50 mM $NaPO_4$, pH 6.5) buffer. Then 1.2 ml of an aqueous sodium periodate solution (10 mM) is added and the mixture is incubated for 1 h in the dark at 4° C. under gentle stirring. Subsequently the reaction is quenched for 15 min at RT by the addition of 600 µl of 1M aqueous glycerol solution. The mixture is subsequently subjected to UF/DF employing a Pellicon XL Ultracel 30 kD membrane.

The UF/DF retentate (63.4 ml), containing oxidized rFIX, is further diluted with 59.6 ml phosphate buffer (50 mM $NaPO_4$, pH 6.0) and mixed with 6.5 ml of an aqueous aniline solution (200 mM) and incubated for 30 min at RT. Then 12.3 ml of the PSA-hydrazide reagent (prepared according Example 16) is added to give a 5 fold molar reagent excess. This mixture is incubated for 2 h at RT in the dark under gentle stirring.

The excess of the PSA-hydrazide reagent and free rFIX is removed by means of HIC. The conductivity of the reaction mixture is raised to 180 mS/cm and loaded onto a column filled with 48 ml Butyl-Sepharose FF (GE Healthcare, Fairfield, Conn.) pre-equilibrated with 50 mM Hepes, 3M sodium chloride, 6.7 mM calcium chloride, 0.01% Tween 80, pH 6.9. Subsequently the conjugate is eluted with 50 mM Hepes, 5 mM calcium chloride, 0.01% Tween 80, pH 7.4. Finally the PSA-rFIX containing fractions are collected and subjected to UF/DF by use of a 30 kD membrane made of regenerated cellulose (Millipore). The preparation is analytically characterized by measuring total protein (BCA) and FIX chromogenic activity. For the PSA-rFIX conjugate a specific activity of >50% in comparison to native rFIX is determined.

Example 18

Polysialylation of rFIX and Purification Using a Two Step Procedure 140 mg rFIX was dissolved in 62 ml phosphate buffer (50 mM $NaPO_4$, pH 6.0) buffer. Then 1.92 ml of an aqueous sodium periodate solution (10 mM) were added and the mixture was incubated for 1 h in the dark at 4° C. under gentle stirring and quenched for 15 min at RT by the addition of 640 of an 1M aqueous glycerol solution. Subsequently the mixture was subjected to UF/DF employing a Pellicon XL Ultracel 30 kD membrane.

The UF/DF retentate (69.4 ml), containing oxidized rFIX, was further diluted with 73.8 ml phosphate buffer (50 mM $NaPO_4$, pH 6.0), mixed with 8.2 ml of an aqueous aniline solution (200 mM) and incubated for 30 min at RT. Then 12.3 ml of the aminooxy reagent (prepared according to Example 3) were added to give a 2.5 fold molar reagent excess. This mixture was incubated for 2.5 h at RT in the dark under gentle stirring.

The free rFIX is removed by means of anion exchange chromatography (AIEC). The reaction mixture is diluted with 20 ml Buffer A (50 mM Hepes, 5 mM $CaCl_2$, pH 7.5) and loaded onto a Q-Sepharose FF 26/10 column (GE Healthcare, Fairfield, Conn.) pre-equilibrated with Buffer A. Then the column is eluted with Buffer B (50 mM Hepes, 1M NaCl, 5 mM $CaCl_2$, pH 7.5). Free rFIX elutes at a conductivity between 12-25 mS/cm and the conjugate between 27-45 mS/cm. The conductivity of the conjugate containing fractions are subsequently raised to 190 mS/cm by addition of Buffer C (50 mM Hepes, 5M NaCl, 5 mM $CaCl_2$, pH 6.9) and loaded onto a Butyl Sepharose FF 26/10 column (GE Healthcare, Fairfield, Conn.) pre-equilibrated with Buffer D (50 mM Hepes, 3M NaCl, 5 mM $CaCl_2$, pH 6.9). Free PSA-reagent is washed out within 5 CV Buffer D. Subsequently the conjugate is eluted with 100% Buffer E (50 mM Hepes, 5 mM $CaCl_2$, pH 7.4). The conjugate containing fractions are concentrated by UF/DF using a 10 kD membrane made of regenerated cellulose (88 $cm^2$, cut-off 10 kD/Millipore). The final diafiltration step is performed against histidine buffer, pH 7.2 containing 150 mM NaCl and 5 mM $CaCl_2$. The preparation is analytically characterized by measuring total protein (BCA) and FIX chromogenic activity. For the PSA-rFIX conjugate a specific activity of >50% in comparison to native rFIX is determined.

Example 19

Coupling of Aminooxy-PSA to rFVIIa and Purification of the Conjugate

A solution of 10 mg rFVIIa in 5 ml reaction buffer (50 mM Hepes, 150 mM sodium chloride, 5 mM calcium chloride, pH 6.0) is mixed with an aqueous solution of $NaIO_4$ (final concentration: 100 µM) and incubated for 1 h at 4° C. under gentle stirring in the dark and quenched by the addition of an aqueous solution of cysteine (final concentration: 1 mM) for 15 min. The reaction mixture is subsequently subjected to UF/DF. To the retentate (10 ml) a 30 fold molar excess of Aminooxy reagent (prepared according to Example 1) is added. The coupling reaction is performed for 2 hours at room temperature in the dark under gentle shaking. The excess of aminooxy reagent is removed by HIC. The conductivity of the reaction mixture is raised to 130 mS/cm by adding a buffer containing ammonium acetate (50 mM Hepes, 350 mM NaCl, 5 mM Calcium chloride, 8 M ammonium acetate, 0.01% Tween 80, pH 6.9) and loaded onto a HiTrap Butyl FF column (5 ml, GE Healthcare, Fairfield, Conn.) pre-equilibrated with 50 mM Hepes, 2.5 M ammonium acetate, 350 mM sodium chloride, 5 mM calcium chloride, 0.01% Tween 80, pH 6.9. Subsequently the conjugate is eluted with 50 mM Hepes, 5 mM calcium chloride, 0.01% Tween 80, pH 7.4 by a linear gradient of 100% elution buffer in 20 CV. Finally the PSA-rFVIIa containing fractions are collected and subjected to UF/DF by use of a 30 kD membrane made of regenerated cellulose (Vivaspin). The preparation is analytically characterized by measuring total protein (BCA) and FVIIa chromogenic activity (Staclot assay, Diagnostica Stago, Asnières, France) and shows a specific activity of >20% compared to the rFVIIa starting material.

Example 20

Coupling of Aminooxy-PSA to rFVIIa in the Presence of Aniline as Nucleophilic Catalyst To 3.0 mg rFVIIa, dissolved in 1.4 ml 50 mM sodium acetate buffer, pH 6.0, 14.10 of an aqueous sodium periodate solution (10 mM) is added. The mixture is shaken in the dark for 1 h at 4° C. and quenched for 15 min at room temperature by the addition of 1.50 µl 1M glycerol. Low molecular weight contaminates are removed by means of size exclusion chromatography (SEC) employing PD-10 desalting columns (GE Healthcare, Fairfield, Conn.). 3 mg oxidized rFVIIa, dissolved in 3 ml 50 mM sodium acetate buffer, pH 6.0 is mixed with aniline (a nucleophilic catalyst, final concentration: 10 mM) and shaken for 30 min at room temperature. Next, aminooxy-PSA is added to give a 5 fold molar excess and the mixture is shaken for 2 hrs at room temperature. Subsequently the excess PSA reagent and free rFIX are removed by means of HIC. The conductivity of the cooled reaction mixture is raised to 180 mS/cm and loaded onto a 5 ml HiTrap Butyl FF (GE Healthcare, Fairfield, Conn.) HIC column (1.6×2.5 cm), pre-equilibrated with 50 mM Hepes, 3M sodium chloride, 6.7 mM calcium chloride, 0.01% Tween 80, pH 6.9. The conjugate is eluted with a linear gradient to 50 mM HEPES, 6.7 mM calcium chloride, 0.005% Tween 80, pH 7.4 in 20 CV with at a flow rate of 5 ml/min.

Example 21

Preparation of an Aminooxy-PEG Reagent

A branched PEG-aldehyde (MW 40 kD) is used for coupling to the diaminooxy linker, which is prepared as described in Example 1. This PEG-aldehyde reagent is available from NOF (NOF Corp., Tokyo, Japan). 500 mg of PEG-aldehyde is dissolved in 8 ml 50 mM sodium acetate buffer, pH 5.5. Then 100 mg 3-oxa-pentane-1,5-dioxyamine is added. After shaking for 2 hrs at room temperature, 44 mg sodium cyanoborohydride is added. After shaking for another 4 hrs at 4° C., the reaction mix is loaded into a Slide-A-Lyzer (Pierce, Rockford, Ill.) dialysis cassette (3.5 kD membrane, regenerated cellulose) and dialyzed against PBS pH 7.2 for 4 days. The product is frozen at −80° C.

Example 22

PEGylation of rFIX with an Aminooxy PEG-Reagent rFIX is PEGylated by use of a linear 20 kD PEGylation reagent containing an aminooxy group. An example of this type of reagent is the Sunbright® CA series from NOF (NOF Corp., Tokyo, Japan). rFIX is oxidized at a protein concentration of 2 mg/ml with $NaIO_4$ (final: concentration: 100 µM) for 1 hour under gentle shaking in the dark at 4° C. in reaction buffer (50 mM Hepes, 150 mM sodium chloride, 5 mM calcium chloride, pH 6.0) and quenched by the addition of an aqueous solution of glycerol (final concentration: 1 mM) for 15 min. The reaction mixture is subsequently subjected to UF/DF. To the retentate a 3 fold molar excess of Aminooxy reagent and aniline (a nucleophilic catalyst, final concentration: 10 mM) are added. The coupling reaction is performed for 2 hours at room temperature in the dark under gentle shaking. Finally the PEG-rFIX conjugate is purified by ion-exchange chromatography on Q-Sepharose FF. 1.5 mg protein/ml gel is loaded on the column pre equilibrated with 50 mM Tris, pH 8.0. The conjugate is eluted with 50 mM Tris and 1 M sodium chloride, pH 8.0 in 20 CV and is then subjected to UF/DF using a 30 kD membrane. The preparation is analytically characterized by measuring total protein (BCA) and FIX chromogenic activity. For the PEG-rFIX conjugate a specific activity of >75% in comparison to native rFIX is determined.

Example 23

PEGylation of rFVIII with an Aminooxy PEG-Reagent rFVIII is PEGylated by use of a linear 20 kD PEGylation reagent containing an aminooxy group. An example of this type of reagent is the Sunbright® CA series from NOF (NOF Corp., Tokyo, Japan). rFVIII is oxidized at a protein concentration of 1 mg/ml with $NaIO_4$ (final: concentration: 100 µM) for 1 hour under gentle shaking in the dark at 4° C. in reaction buffer (50 mM Hepes, 150 mM sodium chloride, 5 mM calcium chloride, pH 6.0) and quenched by the addition of an aqueous solution of cysteine (final concentration: 1 mM) for 15 min. The reaction mixture is subsequently subjected to UF/DF. To the retentate a 20 fold molar excess of Aminooxy reagent and aniline (a nucleophilic catalyst, final concentration: 10 mM) are added. The coupling reaction is performed for 2 hours at room temperature in the dark under gentle shaking. Finally the PEG-rFVIII conjugate is purified by ion-exchange chromatography on Q-Sepharose FF. 1.5 mg protein/ml gel is loaded on the column pre equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using a 30 kD membrane. The analytical characterization of the conjugate by FVIII chromogenic assay and determination of total protein (BCA assay) shows a specific activity of >60% compared to the rFVIII starting material.

Example 24

PEGylation of rFVIIa with an Aminooxy PEG-Reagent rFVIIa is PEGylated by use of a linear 20 kD PEGylation reagent containing an aminooxy group. An example of this type of reagent is the Sunbright® CA series from NOF (NOF Corp., Tokyo, Japan). rFVIIa is oxidized at a protein concentration of 2 mg/ml with $NaIO_4$ (final: concentration: 100 µM) for 1 hour under gentle shaking in the dark at 4° C. in reaction buffer (50 mM Hepes, 150 mM sodium chloride, 5 mM calcium chloride, pH 6.0) and quenched by the addition of an aqueous solution of glycerol (final concentration: 1 mM) for 15 min. The reaction mixture is subsequently subjected to UF/DF. To the retentate a 5 fold molar excess of Aminooxy reagent and aniline (a nucleophilic catalyst, final concentration: 10 mM) are added. The coupling reaction is performed for 2 hours at room temperature in the dark under gentle shaking. Finally the PEG-rFVIIa conjugate is purified by ion-exchange chromatography on Q-Sepharose FF. 1.5 mg protein/ml gel is loaded on the column pre equilibrated with 20 mM Hepes buffer containing 1 mM CaCl$_2$, pH 7.4. The conjugate is eluted with 20 mM Hepes buffer containing 1 mM CaCl$_2$ and 500 mM sodium chloride, pH 7.4 and is then subjected to UF/DF using a 30 kD membrane. The analytical characterization of the conjugate by measuring FVIIa activity (Staclot assay, Diagnostica Stago, Asnières, France) and total protein (BCA) shows a specific activity of >25% compared to the rFVIIa starting material.

Example 25

PEGylation of rFIX with an PEG-Hydrazide Reagent rFIX is PEGylated by use of a linear 20 kD PEGylation reagent containing a hydrazide group. An example of this type of reagent is the Sunbright® HZ series from NOF (NOF Corp., Tokyo, Japan). rFIX is oxidized at a protein concentration of 2 mg/ml with NaIO$_4$ (final: concentration: 100 μM) for 1 hour under gentle shaking in the dark at 4° C. in reaction buffer (50 mM Hepes, 150 mM sodium chloride, 5 mM calcium chloride, pH 6.0) and quenched by the addition of an aqueous solution of glycerol (final concentration: 1 mM) for 15 min. The reaction mixture is subsequently subjected to UF/DF. To the retentate a 50 fold molar excess of Hydrazide reagent and aniline (a nucleophilic catalyst, final concentration: 10 mM) are added. The coupling reaction is performed for 2 hours at room temperature in the dark under gentle shaking. Finally the PEG-rFIX conjugate is purified by ion-exchange chromatography on Q-Sepharose FF. The reaction mixture is loaded onto the column (1.5 mg protein/ml gel), which is preequilibrated with 50 mM Tris-buffer, pH 8.0. The conjugate is eluted with 20 CV Tris-buffer, pH 8.0 (50 mM Tris, 1 M NaCl) and is then subjected to UF/DF using a 30 kD membrane. The preparation is analytically characterized by measuring total protein (BCA) and FIX chromogenic activity. For the PEG-rFIX conjugate a specific activity of >50% in comparison to native rFIX is determined (chromogenic assay).

Example 26

Polysialylation of rFVIII in the Presence of 2 mM Aniline rFVIII is transferred into reaction buffer (50 mM Hepes, 350 mM sodium chloride, 5 mM calcium chloride, 0.01% TWEEN® 80, pH 6), diluted to a protein concentration of 1 mg/ml and oxidized with NaIO$_4$ (final: concentration: 100 μM) for 1 hour under gentle shaking in the dark at 4° C. in reaction buffer (50 mM Hepes, 150 mM sodium chloride, 5 mM calcium chloride, pH 6.0) and quenched by the addition of an aqueous solution of cysteine (final concentration: 1 mM) for 15 mM. The reaction mixture is subsequently subjected to UF/DF. To the retentate a 20 fold molar excess of Aminooxy reagent and aniline (a nucleophilic catalyst, final concentration: 2 mM) are added. The coupling reaction is performed for 2 hours at room temperature in the dark under gentle shaking. The excess of aminooxy reagent is removed by means of HIC. The conductivity of the reaction mixture is raised to 130 mS/cm by adding a buffer containing ammonium acetate (50 mM Hepes, 350 mM sodium chloride, 5 mM calcium chloride, 8 M ammonium acetate, 0.01% TWEEN® 80, pH 6.9) and loaded onto a column filled with 53 ml Butyl-Sepharose FF (GE Healthcare, Fairfield, Conn.) pre-equilibrated with 50 mM Hepes, 2.5 M ammonium acetate, 350 mM sodium chloride, 5 mM calcium chloride, 0.01% TWEEN® 80, pH 6.9. Subsequently the conjugate is eluted with 50 mM Hepes, 5 mM calcium chloride, 0.01% TWEEN® 80, pH 7.4 Finally the PSA-rFIX containing fractions are collected and subjected to UF/DF by use of a 30 kD membrane made of regenerated cellulose (Millipore, Billerica, Mass.). The preparation is analytically characterized by measuring total protein (BCA) and FVIII chromogenic activity. For the PSA-rFVIII conjugate a specific activity of 80% in comparison to native rFVIII is determined.

Example 27

Polysialylation of rFVIII in the Presence of 10 mM Aniline rFVIII is transferred into reaction buffer (50 mM Hepes, 350 mM sodium chloride, 5 mM calcium chloride, 0.01% Tween 80, pH 6), diluted to a protein concentration of 1 mg/ml and oxidized with NaIO$_4$ (final: concentration: 100 μM) for 1 hour under gentle shaking in the dark at 4° C. in reaction buffer (50 mM Hepes, 150 mM sodium chloride, 5 mM calcium chloride, pH 6.0) and quenched by the addition of an aqueous solution of cysteine (final concentration: 1 mM) for 15 mM. The reaction mixture is subsequently subjected to UF/DF. To the retentate a 20 fold molar excess of Aminooxy reagent and aniline (a nucleophilic catalyst, final concentration: 10 mM) are added. The coupling reaction is performed for 2 hours at room temperature in the dark under gentle shaking. The excess of aminooxy reagent is removed by means of HIC. The conductivity of the reaction mixture is raised to 130 mS/cm by adding a buffer containing ammonium acetate (50 mM Hepes, 350 mM sodium chloride, 5 mM calcium chloride, 8 M ammonium acetate, 0.01% TWEEN® 80, pH 6.9) and loaded onto a column filled with 53 ml Butyl-Sepharose FF (GE Healthcare, Fairfield, Conn.) pre-equilibrated with 50 mM Hepes, 2.5 M ammonium acetate, 350 mM sodium chloride, 5 mM calcium chloride, 0.01% TWEEN® 80, pH 6.9. Subsequently the conjugate is eluted with 50 mM Hepes, 5 mM calcium chloride, 0.01% TWEEN® 80, pH 7.4. Finally the PSA-rFIX containing fractions are collected and subjected to UF/DF by use of a 30 kD membrane made of regenerated cellulose (Millipore, Billerica, Mass.). The preparation is analytically characterized by measuring total protein (BCA) and FVIII chromogenic activity. For the PSA-rFVIII conjugate a specific activity of 80% in comparison to native rFVIII is determined.

Example 28

PEGylation of a Blood Coagulation Protein Using Branched PEG

PEGylation of a blood coagulation proteins (such as FIX, FVIII and FVIIa as described in Examples 22-25) may be extended to a branched or linear PEGylation reagent as described in Example 21, which is made of an aldehyde and a suitable linker containing an active aminooxy group.

The invention claimed is:

1. A method of preparing a modified blood coagulation protein, comprising: contacting an activated water soluble polymer to an oxidized carbohydrate moiety of a blood coagulation protein under conditions that allow conjugation;
    said blood coagulation protein is selected from the group consisting of
        i) a blood coagulation protein with Factor IX (FIX) biological activity; and
        ii) a blood coagulation protein with Factor VIII (FVIII) biological activity;
    said activated water soluble polymer comprises an active aminooxy linker and a water soluble polymer, wherein said water soluble polymer is selected from the group consisting of polysialic acid (PSA), polysaccharides, pullulan, chitosan, hyaluronic acid, chondroitin sulfate, dermatan sulfate, starch, polyoxazoline, polyacryloylmorpholine, and polyphosphazene; and
    said carbohydrate moiety is oxidized by incubation with a buffer comprising an oxidizing agent selected from the group consisting of sodium periodate ($NaIO_4$), lead tetraacetate ($Pb(OAc)_4$) and potassium perruthenate ($KRuO_4$); wherein an oxime linkage is formed between the oxidized carbohydrate moiety and the active aminooxy linker on the activated water soluble polymer.

2. The method of claim 1, wherein the water soluble polymer is PSA.

3. The method of claim 2, wherein the PSA is comprised of about 10-300 sialic acid units.

4. The method of claim 1, wherein the blood coagulation protein has FIX biological activity.

5. The method of claim 1, wherein the blood coagulation protein has FVIII biological activity.

6. The method of claim 1, wherein the oxidizing agent is sodium periodate ($NaIO_4$).

7. The method of claim 1, wherein the oxidized carbohydrate moiety of the blood coagulation protein is located in the activation peptide of the blood coagulation protein.

8. The method of claim 1, wherein the activated water soluble polymer is activated PSA, and said activated PSA is prepared by reacting an activated aminooxy linker with oxidized PSA;
    wherein the activated aminooxy linker is selected from the group consisting of:
    a) a 3-oxa-pentane-1,5-dioxyamine linker of the formula:

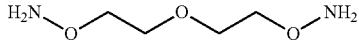

and
    b) a 3,6,9-trioxa-undecane-1,11-dioxyamine linker of the formula:

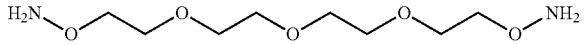

wherein the PSA is oxidized by incubation with an oxidizing agent to form a terminal aldehyde group at the non-reducing end of the PSA.

9. The method of claim 8, wherein the activated aminooxy linker is 3-oxa-pentane-1,5-dioxyamine.

10. The method of claim 8, wherein the oxidizing agent is $NaIO_4$.

11. The method of claim 1, wherein the contacting of the oxidized carbohydrate moiety with the activated water soluble polymer occurs in a buffer comprising a nucleophilic catalyst which is aniline.

12. The method of claim 1, further comprising the step of reducing an oxime linkage in the modified blood coagulation protein by incubating the modified blood coagulation protein in a buffer comprising a reducing compound selected from the group consisting of sodium cyanoborohydride ($NaCNBH_3$) and ascorbic acid (vitamin C).

13. The method of claim 12, wherein the reducing compound is sodium cyanoborohydride ($NaCNBH_3$).

14. The method of claim 1, wherein said modified blood coagulation protein has a specific activity of at least 50% relative to an unmodified blood coagulation protein.

15. The method of claim 1, wherein said modified blood coagulation protein has a specific activity of at least 60% relative to an unmodified blood coagulation protein.

16. The method of claim 1, wherein said modified blood coagulation protein has a specific activity of at least 70% relative to an unmodified blood coagulation protein.

17. The method of claim 1, wherein the linker comprises 1-50 ethylene glycol units.

18. The method of claim 1, wherein the linker has 2 or 4 ethylene glycol units.

19. The method of claim 2, wherein the PSA is comprised of 5-500 sialic acid units.

20. The method of claim 2, wherein the PSA has a molecular weight from 2,000 Da to 45,000 Da.

21. The method of claim 2, wherein the PSA has a molecular weight from 3,000 Da to 35,000 Da.

22. The method of claim 2, wherein the PSA has a molecular weight from 5,000 Da to 25,000 Da.

23. The method of claim 1, wherein the oxidized carbohydrate moiety of the blood coagulation protein is located in the activation peptide of the blood coagulation protein.

24. The method of claim 1, wherein the blood coagulation protein is a full-length blood coagulation protein.

25. The method of claim 1, wherein the blood coagulation protein has FVIII biological activity and is a full-length FVIII.

26. The method of claim 3, wherein the blood coagulation protein has FVIII biological activity, the linker comprises 1-50 ethylene glycol units, wherein the oxidizing agent is sodium periodate ($NaIO_4$).

27. The method of claim 3, wherein the blood coagulation protein has FVIII biological activity, the linker has 2 or 4 ethylene glycol units, wherein the oxidizing agent is sodium periodate ($NaIO_4$).

28. The method of claim 1, wherein the blood coagulation protein has FVIII biological activity, the water soluble polymer is PSA having a molecular weight from 3,000 Da to 35,000 Da, wherein the linker comprises 1-50 ethylene glycol units, wherein the oxidizing agent is sodium periodate ($NaIO_4$).

29. The method of claim 1, wherein the blood coagulation protein has FVIII biological activity, the water soluble polymer is PSA having a molecular weight from 3,000 Da to 35,000 Da, wherein the linker has 2 or 4 ethylene glycol units, wherein the oxidizing agent is sodium periodate ($NaIO_4$).

30. The method of claim 1, wherein the blood coagulation protein has FVIII biological activity and is a full-length FVIII, wherein the water soluble polymer is PSA having a molecular weight from 3,000 Da to 35,000 Da, wherein the linker comprises 1-50 ethylene glycol units, wherein the oxidizing agent is sodium periodate ($NaIO_4$).

31. The method of claim 1, wherein the blood coagulation protein has FVIII biological activity and is a full-length FVIII, wherein the water soluble polymer is PSA having a molecular weight from 3,000 Da to 35,000 Da, wherein the linker has 2 or 4 ethylene glycol units, wherein the oxidizing agent is sodium periodate ($NaIO_4$).

32. The method of claim 3, wherein the blood coagulation protein has FIX biological activity, the linker comprises 1-50 ethylene glycol units, wherein the oxidizing agent is sodium periodate ($NaIO_4$).

33. The method of claim 3, wherein the blood coagulation protein has FIX biological activity, the linker has 2 or 4 ethylene glycol units, wherein the oxidizing agent is sodium periodate ($NaIO_4$).

34. The method of claim 1, wherein the blood coagulation protein has FIX biological activity, the water soluble polymer is PSA having a molecular weight from 3,000 Da to 35,000 Da, wherein the linker comprises 1-50 ethylene glycol units, wherein the oxidizing agent is sodium periodate ($NaIO_4$).

35. The method of claim 1, wherein the blood coagulation protein has FIX biological activity, the water soluble polymer is PSA having a molecular weight from 3,000 Da to 35,000 Da, wherein the linker has 2 or 4 ethylene glycol units, wherein the oxidizing agent is sodium periodate ($NaIO_4$).

\* \* \* \* \*